United States Patent
Yang

(10) Patent No.: US 11,713,445 B2
(45) Date of Patent: Aug. 1, 2023

(54) CURVATURE-DEFINED CONCAVE AND CONVEX PDMS SURFACES FOR USE IN CELL AND TISSUE CULTURING AND IN OTHER SURFACE AND INTERFACE APPLICATIONS

(71) Applicant: Shengyuan Yang, Arlington, MA (US)

(72) Inventor: Shengyuan Yang, Arlington, MA (US)

( * ) Notice: Subject to any disclaimer, the term of this patent is extended or adjusted under 35 U.S.C. 154(b) by 828 days.

(21) Appl. No.: 16/713,644

(22) Filed: Dec. 13, 2019

(65) Prior Publication Data
US 2021/0180012 A1 Jun. 17, 2021

(51) Int. Cl.
*B29C 39/02* (2006.01)
*C12N 5/00* (2006.01)
*B29C 39/10* (2006.01)
*B29K 83/00* (2006.01)

(52) U.S. Cl.
CPC .......... *C12N 5/0075* (2013.01); *B29C 39/026* (2013.01); *B29C 39/10* (2013.01); *B29K 2083/00* (2013.01); *C12N 2531/00* (2013.01); *C12N 2533/30* (2013.01); *C12N 2535/00* (2013.01); *C12N 2537/00* (2013.01); *C12N 2539/00* (2013.01)

(58) Field of Classification Search
None
See application file for complete search history.

(56) References Cited

PUBLICATIONS

Chen et al., Chinese Chemical Letters 28 (2017) 818-826 (Year: 2017).*
Cho et al., BioTechiques, vol. 48, No. 1 (Jan. 2010), pp. 47-52 (Year: 2010).*
Lee et al., Rev. Sci. Instrum. 83, 094302 (2012), 7 pages (Year: 2012).*

* cited by examiner

*Primary Examiner* — Evelyn Y Pyla

(57) ABSTRACT

The present disclosure provides a method of fabricating curvature-defined (C-D) or shape-defined (S-D) concave and convex polydimethylsiloxane (PDMS) surfaces and a method of fabricating C-D or S-D convex and concave gel surfaces for use in cell and tissue culturing and in other surface and interface applications, and provides a method of using C-D or S-D convex and concave surfaces with varying curvatures to direct cell attachment, spreading, and migration.

20 Claims, 14 Drawing Sheets e     peel off the upper newly-solidified layer of PDMS in step d

C-D concave spherical PDMS surfaces (obtained by using the casting-onto and peeling-off fabrication process)

f     pour PDMS mixture concave spherical PDMS surfaces (obtained in step e)

g     peel off the upper newly-solidified layer of PDMS in step f obtained C-D convex spherical PDMS surfaces h  keep  remove  PDMS i  C-D convex spherical surfaces (SSs) of the MGBs  exposed C-D concave spherical PDMS surfaces j  pour PDMS mixture on top of the surfaces obtained in step i

PDMS a2 a3 b2 b3

CURVATURE-DEFINED CONCAVE AND CONVEX PDMS SURFACES FOR USE IN CELL AND TISSUE CULTURING AND IN OTHER SURFACE AND INTERFACE APPLICATIONS

Abbreviations: 3D, three-dimensional; AFM, atomic force microscopy; C-D, curvature-defined; hMSCs, human mesenchymal stem cells; MGB, micro glass ball; PA, polyacrylamide; PDMS, polydimethylsiloxane; RT-PCR, real-time polymerase chain reaction; S-D, shape-defined; SS, spherical surface.

CROSS-REFERENCE TO RELATED APPLICATIONS

This application is related to co-pending U.S. patent application Ser. No. 16/713,756, filed on Dec. 13, 2019, entitled "Curvature-defined convex and concave gel surfaces for use in cell and tissue culturing and in other surface and interface applications," and co-pending U.S. patent application Ser. No. 16/713,889, filed on Dec. 13, 2019, entitled "Methods of using curvature-defined surfaces with varying curvatures to direct cell attachment, spreading, and migration," both of which are incorporated herein by reference in their entireties.

BACKGROUND

Increasing evidences have shown that mechanical factors have profound influences on cellular biochemical and biological behaviors, but the relevant studies in cell mechanobiology are far from being systematic or well-documented. Substrate geometries, which belong to mechanical factors, have been shown to influence and induce stem cell differentiation. These substrate geometries mainly include the planar geometrically defined micro-patterns (Kilian et al., 2010; Wan et al., 2010; Song et al., 2011; Yao et al., 2013; Bao et al., 2018; von Erlach et al., 2018) and the non-planar nanotopographies (Dalby et al., 2007; Ankam et al., 2013; Song et al., 2016; Vega et al., 2018; Zhao et al., 2018). Motivated by the necessity to study the behavioral responses of cells growing on curved surfaces (Baptista et al., 2019), a few methods, including sucking a thin polydimethylsiloxane (PDMS) membrane through a shadow mask (Park et al., 2009), thermal reflow of photoresist (Soscia et al., 2013), and stereolithography and the after slowly-shrinking (Werner et al., 2017), have been developed to fabricate convex and concave microstructures to culture cells. However, these methods cannot precisely control the geometrical shapes of the surfaces of the fabricated convex and concave microstructures, and the shapes of the surfaces of these fabricated convex and concave microstructures are not necessarily spherical and the curvatures of the surfaces of these fabricated microstructures normally cannot be precisely known or defined. It is also very problematic to use these methods to fabricate convex and concave microstructures at larger or millimeter scales for cellular studies.

Micro Glass Ball (MGB) Embedded Polyacrylamide (PA) Gels—

The inventor of the present disclosure was granted a U.S. Patent (U.S. Pat. No. 8,802,430, Date of Patent: Aug. 12, 2014, entitled "Micro and nano glass balls embedded in a gel presenting micrometer and nanometer scale curvature and stiffness patterns for use in cell and tissue culturing and a method for making same") for the invention of a class of curvature-defined (C-D) or shape-defined (S-D) substrates, micro glass ball (MGB) embedded polyacrylamide (PA) gels, for cell culturing. Since the inventor of U.S. Pat. No. 8,802,430 and the inventor of the present disclosure are the same person, in the below, to simply the writing, the inventor of both U.S. Pat. No. 8,802,430 and the present disclosure is called the inventor. The inventor of both U.S. Pat. No. 8,802,430 and the present disclosure is also the applicant of both U.S. Pat. No. 8,802,430 and the present disclosure. In an invented substrate in U.S. Pat. No. 8,802,430, the PA gel is used to immobilize the MGBs. Before the polymerization of the PA solution, the MGBs with diameters for the desired studies were pressed into the surface of the PA solution. After the polymerization of the PA solution, the MGBs were immobilized or embedded on the surface of the formed PA gel, and the exposed parts of the embedded MGBs from the surface of the PA gel were used as the convex microstructures to culture cells. The three-dimensional (3D) shape of the surface of a MGB is spherical and is well-defined, and the principal curvature at any point on the surface of a ball is the same and calculated as the inverse of the radius of this ball's spherical surface (SS) (i.e., the inverse of the radius of this ball). For this situation of curved-surfaces with well-defined shapes, the principal curvatures at any point on such a surface can be readily obtained by using the results in differential geometry, and therefore, the curved-surfaces with well-defined shapes are also C-D, i.e., an S-D surface is also C-D. Thus, in the present disclosure and/or patent application, C-D and S-D indicate the same meaning, and to stress and/or to remind both the C-D and S-D nature of a curved-surface with a well-defined shape, the phrases "C-D" and "S-D" appear at the same time in the format of "C-D or S-D" in the writing, especially in the writing of the claims, to describe a curved-surface with a well-defined shape. Then MGB embedded PA gels have C-D or S-D surfaces. But, to simply the writing, in the below, when the stressing and/or reminding effects are unnecessary, the phrase "C-D" is used to serve the purposes of the phrase "C-D or S-D". Here, for cell culturing, substrates having C-D surfaces are called C-D substrates, and MGB embedded PA gels are C-D substrates.

The invented method, in U.S. Pat. No. 8,802,430, of making C-D substrates by immobilizing the microstructures, such as the MGBs, with well-defined surface shapes and surface curvatures in polymerizing gels, ingeniously avoids the difficulty of fabricating microstructures with C-D surfaces of the other developed methods that directly fabricate on the surfaces of the substrates. The other vital advantage of this method is that it virtually has no limits on the sizes of the microstructures that it immobilizes, i.e., this method virtually has no limits on the range of the generated surface curvatures for cell studies. To date, the diameters of the glass balls that we have used to make MGB embedded PA gels were from 5 m to 6 mm. While the surface of a glass ball with a diameter of several millimeters is virtually flat with respect to the size of a cell, the small surface curvatures of the glass balls with diameters of several millimeters can have profound effects on stem cell behaviors, as shown in our experimental results on human mesenchymal stem cells (hMSCs) (Lee and Yang, 2017). The effects of substrate curvatures (i.e., the surface curvatures of the substrates) at this small scale, or the effects of curved substrates with diameters at the millimeter scale, on cellular behaviors have also not been investigated before. Therefore, due to its C-D nature and wide-range-of-curvature-coverage nature, this class of substrates, MGB embedded PA gels, provides a unique and effective tool and opens up a systematic paradigm for the studies of cell mechanobiological responses to substrate curvatures and their related applications.

Cell Experimental Findings—

We have cultured NIH-3T3 fibroblasts and hMSCs on these MGB embedded PA gels (Lee and Yang, 2012; Lee and Yang, 2017). We found that, as expected, overall both the cell attachment rate and mean cell spread area of both cell types decreased with the decrease of the substrate ball diameter. But, the sensitivities of the attachment and spreading morphology of an hMSC to substrate curvature were very different from those of a fibroblast. Specifically, (1) Among the used diameters, the minimum diameter of a glass ball on which an NIH-3T3 fibroblast can attach and spread, without wrapping over the ball, was 58 m, whereas the minimum diameter of a glass ball on which an hMSC can attach and spread was 500 m. This indicates that the attachment of an hMSC is much more sensitive to the large surface curvatures of the small substrate balls than that of a fibroblast. (2) The spreading morphologies of the fibroblasts on the 2 mm-balls were almost indistinguishable from those of the fibroblasts on the flat glass plates, but the hMSCs on the 4 mm-balls were majorly spindle-shaped with only two lamellipodia while the hMSCs on flat plates were well-spread with randomly multiple lamellipodia. This indicates that the spreading morphology of an hMSC is much more sensitive to the small surface curvatures of the large substrate balls than that of a fibroblast. (3) The hMSCs on the balls with diameters from 4 mm to 500 m were always majorly spindle-shaped with only two lamellipodia, whereas the morphologies of the fibroblasts varied from the well-spread shapes on the 2 mm-balls to the round-shapes on the 500 m-balls. This indicates that the spreading morphology of a fibroblast is much more sensitive to the intermediate surface curvatures of the intermediately-sized substrate balls than that of an hMSC.

Due to the abrupt change in spreading morphology, from the well-spread shapes on the flat plates to the spindle shapes on the MGBs, of the hMSCs, and due to the decreased mean cell spread area of the hMSCs with the decrease of the substrate ball diameter, we say that, the curvatures of the substrates restricted the spreading of the hMSCs and this restriction was larger when the substrate curvature was larger. Based on the related reports on substrate geometries (Kilian et al., 2010; Wan et al., 2010; Song et al., 2011; Yao et al., 2013; Bao et al., 2018; von Erlach et al., 2018) and substrate matrix elasticity (Engler et al., 2006; Swift et al., 2013; Ivanovska et al., 2015) and substrate rigidity (Fu et al., 2010) influencing and inducing stem cell differentiation, it is very reasonable for us to hypothesize that substrate curvatures influence and induce stem cell differentiation. Therefore, we conducted the real-time polymerase chain reaction (RT-PCR) analysis to quantify the relative osteogenic and adipogenic gene expressions of the hMSCs growing on the MGBs. Without the corresponding differentiation induction media, with respect to the corresponding gene expressions of the hMSCs growing on the flat plates, we did not find any significant osteogenic gene expression for all the hMSCs growing on the MGBs, but we found that there was significant adipogenesis for the hMSCs growing on the 1.1 mm-, 900 µm-, 750 µm-, and 500 µm-balls, and the hMSCs growing on the 2 mm-, 3 mm-, and 4 mm-balls, and on the flat plates had negligible adipogenesis. Thus, adipogenesis of hMSCs can be induced purely by appropriate substrate curvatures, i.e., substrate curvatures alone can induce stem cell differentiation. We also found that, the variation of the relative adipogenic gene expression of the hMSCs with the diameter of the substrate ball was not monotonic, and there was no obvious trend of this variation with the diameter of the substrate ball.

Because of the above significant experimental findings on the hMSCs growing on the curved substrates (i.e., the MGBs), as discussed in Ref. (Lee and Yang, 2017) and its online supporting information, it is necessary to carry out the substrate curvature-related systematic experimental and theoretical studies for the development of stem cell mechanobiology which has vast applications in tissue engineering and regenerative medicine (Ivanovska et al., 2015; Vining and Mooney, 2017).

Concave Spherical P A Gel Surfaces—

Note that the MGB embedded PA gels only present the C-D convex SSs. Exposed concave spherical PA gel surfaces may be obtained by carefully-removing the embedded MGBs from the MGB embedded PA gels. In our experiments, we have tried this removing process of the embedded MGBs and have observed the exposed concave PA gel surfaces, which showed that this removing process presents a method to make non-planar concave PA gel surfaces which may be highly-desirable for some cellular studies since planar PA gels are commonly used as the soft culturing substrates to study cell mechanics and mechanobiology (Wang and Pelham, 1998; Lo et al., 2000; Engler et al., 2006; Buxboim et al., 2010; Rape et al., 2011; Tang et al., 2012; Aragona et al., 2013; Colin-York et al., 2017; Charrier et al., 2018). After an embedded MGB is removed from a MGB embedded PA gel, ideally, we expect that the shape of the exposed concave SS of the PA gel (due to the removing of this embedded ball) is an exact replica of that of the C-D convex SS of this removed ball. But, due to the strong viscoelastic material behaviors of PA gels (which are hydrogels), the possible significant pulling and pushing forces between an embedded MGB and the PA gel material during the removing process of this ball may induce undesirable significant permanent deformations on the to-be-exposed concave SS of the PA gel, and then after this ball is removed, the shape of the final exposed concave SS of the PA gel may differ significantly from an exact replica of that of the C-D convex SS of this removed ball. If there are significant permanent deformations on the to-be-exposed concave SS of the PA gel due to the possible significant pulling and pushing forces, a simple qualitative analysis will show that the final concave shape of the exposed SS of the PA gel should be a little flattened compared with an exact replica of the shape of the convex SS of the corresponding removed ball. Also, in our experiments we observed that the PA gels were significantly swollen at 37° C. (in the incubator) compared with the same PA gels at room temperature. Then, due to the possible non-uniform swelling and shrinking in the PA gel material induced by various reasons, the shape of the exposed concave SS of the PA gel (after the removal of an embedded MGB) may vary significantly with temperature changes. These two possible sources of significant shape deviation of the exposed concave SS of a PA gel due to the removal of an embedded MGB, with respect to an exact replica of the shape of the convex SS of this removed ball, will compromise the trustworthiness of the obtained quantitative cellular responses to substrate curvatures if we treat the exposed concave SS of this PA gel as a C-D SS with the radius of the corresponding removed ball. This motivated the invention of the present patent application.

Moreover, due to its ideal properties such as nontoxicity, biocompatibility, blood compatibility, elasticity, transparency, and durability (Subramaniam and Sethuraman, 2014), the elastomer material, PDMS, is widely used to fabricate various microstructures for cellular studies (Park et al., 2009; Fu et al., 2010; Fernandes et al., 2013; Soscia et al., 2013; Irimia, 2014; Lee et al., 2018). However, to date a method to fabricate C-D or S-D concave and/or convex PDMS microstructures or surfaces has not been developed for use in cell and tissue culturing and in other surface and interface applications, which also motivated the invention of the present patent application.

BRIEF SUMMARY

The present disclosure provides a method of fabricating C-D or S-D concave and convex PDMS surfaces and a method of fabricating C-D or S-D convex and concave gel surfaces for use in cell and tissue culturing and in other surface and interface applications, and provides a method of using C-D or S-D convex and concave surfaces with varying curvatures to direct cell attachment, spreading, and migration.

In the first aspect, the disclosure provides a method of fabricating C-D or S-D concave and convex surfaces for use in cell and tissue culturing and in other surface and interface applications, comprising: embedding rigid C-D or S-D convex microstructures on a solidified first material layer of a sufficient rigidity through the polymerization process to form this solidified first material layer, and then the exposed C-D or S-D concave surfaces being obtained by carefully-removing these embedded rigid C-D or S-D convex microstructures from this solidified first material layer; the exposed C-D or S-D concave surfaces also being obtained by taking advantage of the C-D or S-D convex surfaces of the exposed parts of the embedded rigid convex microstructures on the first material layer of a sufficient rigidity through using the casting-onto and peeling-off fabrication process; and, by using the casting-onto and peeling-off fabrication process onto the obtained C-D or S-D concave surfaces, a substrate of a sufficient rigidity having C-D or S-D convex surfaces being obtained, and so forth.

Specifically, when the material PDMS is the solidified first material layer of a sufficient rigidity in the above invented method of fabricating C-D or S-D concave and convex surfaces of the first aspect of the disclosure, the disclosure provides a method of fabricating C-D or S-D concave and convex PDMS surfaces for use in cell and tissue culturing and in other surface and interface applications.

More specifically, when the rigid C-D or S-D convex microstructures embedded on the solidified first PDMS material layer in the above invented method of fabricating C-D or S-D concave and convex PDMS surfaces of the first aspect of the disclosure are rigid C-D or S-D convex spherical microstructures, the disclosure provides a method of fabricating C-D or S-D concave and convex spherical PDMS surfaces for use in cell and tissue culturing and in other surface and interface applications.

In the various embodiments of the invented methods in the first aspect of the disclosure, the shapes and/or curvatures, and sizes of the rigid C-D or S-D convex microstructures embedded on the solidified first material layer of a sufficient rigidity can be same or different. Then, the shapes and/or curvatures, and sizes of the final fabricated C-D or S-D concave and convex surfaces can be same or different.

In the various embodiments of the invented methods in the first aspect of the disclosure, the sizes of the rigid C-D or S-D convex microstructures embedded on the solidified first material layer of a sufficient rigidity can range from about one nanometer to about several centimeters or above. Then, the sizes of the final fabricated C-D or S-D concave and convex surfaces can range from about one nanometer to about several centimeters or above.

In some embodiments of the invented methods in the first aspect of the disclosure, the rigid C-D or S-D convex microstructures are embedded on the solidified first material layer of a sufficient rigidity as an array or arrays, or as a micro-array or micro-arrays, or as a pattern or patterns, or as a micro-pattern or micro-patterns. Then, the final fabricated C-D or S-D concave and convex surfaces are arranged as the same array or arrays, or as the same micro-array or micro-arrays, or as the same pattern or patterns, or as the same micro-pattern or micro-patterns.

In the second aspect, the disclosure provides a method of fabricating C-D or S-D convex and concave spherical gel surfaces for use in cell and tissue culturing and in other surface and interface applications, comprising: a first substrate of a sufficient rigidity having a C-D or S-D convex spherical surface (SS) of a desired radius r, coated with an appropriate chemical adhesive agent to ensure the strong adherence of the to-be-formed gel layer to this convex SS, or coated with an appropriate chemical repellent agent to ensure this first substrate can be easily withdrawn from the to-be-exposed concave gel surface coated on the concave SS of the following second substrate; a second substrate of a sufficient rigidity having a C-D or S-D concave SS of the radius r plus the thickness of the to-be-coated gel layer, coated with an appropriate chemical repellent agent to ensure this second substrate can be easily withdrawn or detached from the to-be-exposed convex gel surface coated on the convex SS of the first substrate, or coated with an appropriate chemical adhesive agent to ensure the strong adherence of the to-be-formed gel layer to this concave SS; depending on the thickness of the gel layer to be coated on the C-D or S-D convex SS of the first substrate or on the C-D or S-D concave SS of the second substrate, an appropriate amount of the gel solution being dropped onto the C-D or S-D convex SS of the first substrate or onto the C-D or S-D concave SS of the second substrate;

the first and second substrates being oriented and precisely aligned with each other so that the centerline of the C-D or S-D concave SS of the second substrate and the centerline of the C-D or S-D convex SS of the first substrate are precisely aligned with each other; the second substrate or the first substrate then being brought to approach to the first substrate or the second substrate to press the gel solution to uniformly re-distribute the gel solution on the C-D or S-D convex SS of the first substrate or on the C-D or S-D concave SS of the second substrate; and, after the second substrate or the first substrate is carefully withdrawn from the first substrate or the second substrate, the C-D or S-D convex SS of the first substrate or the C-D or S-D concave SS of the second substrate being coated with the gel layer of a uniform thickness, wherein the first substrate or the second substrate become a substrate with a C-D or S-D convex spherical gel surface or a substrate with a C-D or S-D concave spherical gel surface.

In some embodiments of the invented method in the second aspect of the disclosure, the first substrate of a sufficient rigidity has an array or arrays of C-D or S-D convex SSs each of which has same radius or different radii, a second substrate of a sufficient rigidity having an array or arrays of C-D or S-D concave SSs, wherein the pattern of the array or arrays of the C-D or S-D concave SSs is identical to that of the array or arrays of C-D or S-D convex SSs of the first substrate, and each of these C-D or S-D concave SSs has the radius equal to the radius of the corresponding C-D or S-D convex SS of the first substrate plus the corresponding thickness of the to-be-coated gel layer on this C-D or S-D convex SS of the first substrate.

In the third aspect, the disclosure provides three methods of using C-D or S-D convex and concave surfaces with varying curvatures to direct cell attachment, spreading, and migration, respectively comprising: culturing a cell on a substrate with a smooth revolution surface, having the shape-variation setting of from a circular flat surface to a curved surface, in the presence of cell culture media, wherein the attachment, spreading, and migration of this cell are confined in the circular flat part by the curved part of this smooth revolution surface; culturing a cell on a substrate with a smooth cylindrical surface, having the shape-variation setting of from a rectangular flat surface to two curved surfaces that are respectively located at the two longitudinal sides of the rectangular flat surface, in the presence of cell culture media, wherein the attachment, spreading, and migration of this cell are confined in the rectangular flat part by the two curved parts (that are respectively located at the two longitudinal sides of the rectangular flat part) of this smooth cylindrical surface; and, culturing a cell on a substrate with a smooth cylindrical surface, having the shape-variation setting of from a curved surface with a defined curvature to another curved surface with a defined different curvature, in the presence of cell culture media, wherein the confinement of the curved surface with the larger curvature of the smooth cylindrical surface of the substrate to the attachment, spreading, and migration of this cell is larger compared with that of the other curved surface with the smaller curvature of the smooth cylindrical surface of the substrate.

In some embodiments of the invented methods in the third aspect of the disclosure, the substrate comprises an array of substrates each of which has a smooth revolution surface having the corresponding shape-variation setting.

The invented methods described in the present disclosure can be used in connection with pharmaceutical, medical, veterinary, and engineering applications, as well as fundamental scientific research and methodologies, as would be identifiable by a skilled person upon reading of the present disclosure. These and other objects, features and advantages of the present disclosure will become clearer when the drawings, as well as the detailed description, are taken into consideration.

BRIEF DESCRIPTION OF THE DRAWINGS

For a fuller understanding of the nature of the present disclosure, reference to the following detailed description should be taken in connection with the accompanying figures.

DETAILED DESCRIPTION OF THE DISCLOSURE

Figure 1:
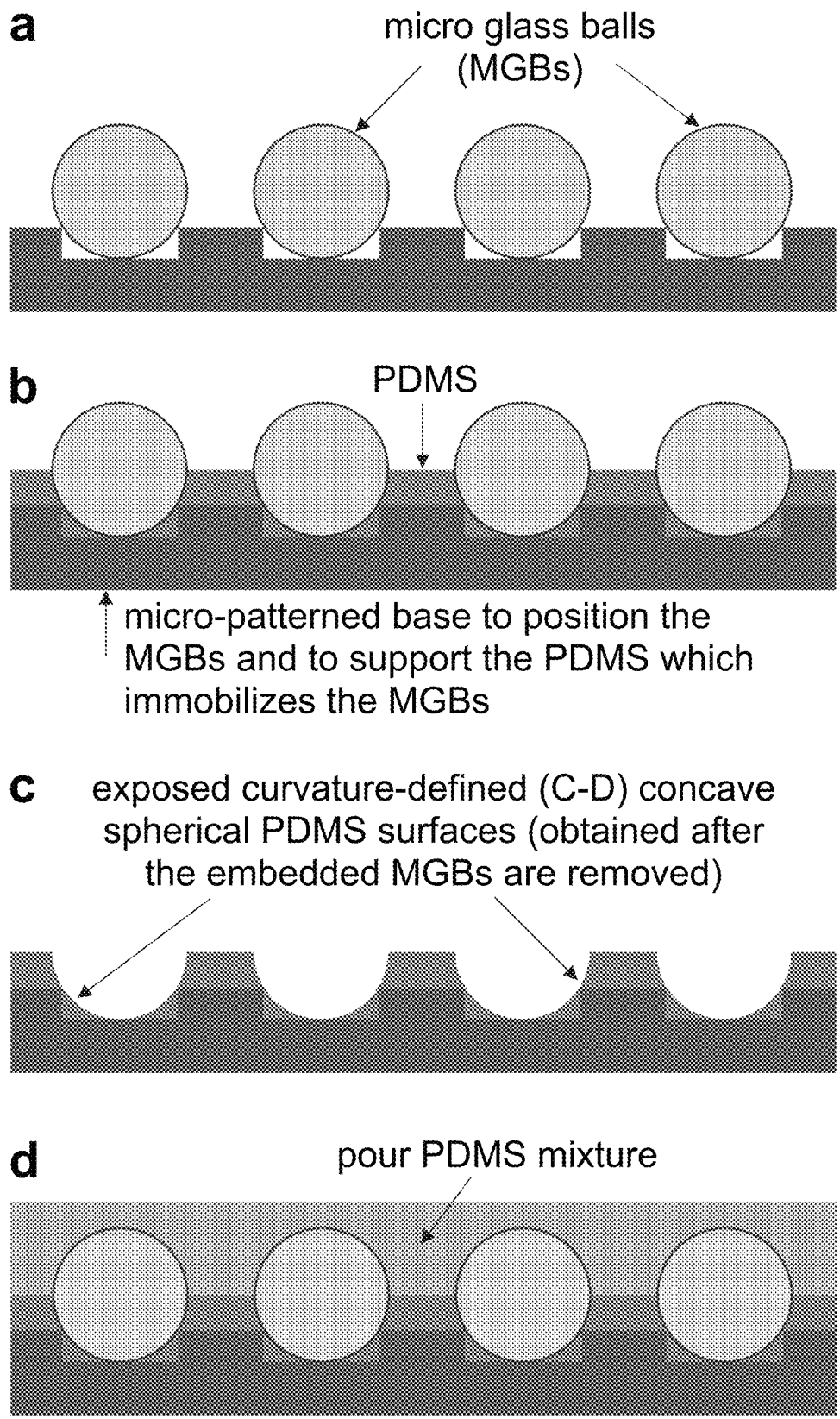
FIG. 1 illustrates a MGB embedded PDMS substrate and the subsequent fabrication processes to obtain C-D or S-D concave and convex spherical PDMS surfaces according to the present invention.
Figure 1:
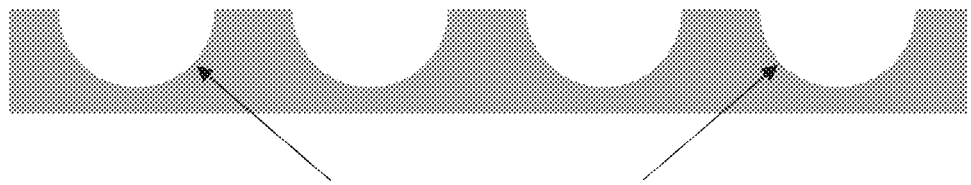
Figure 1:
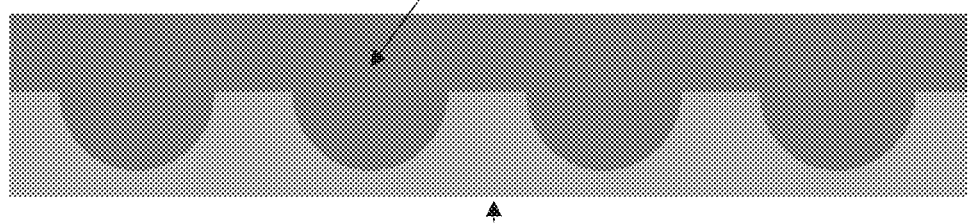
Figure 1:
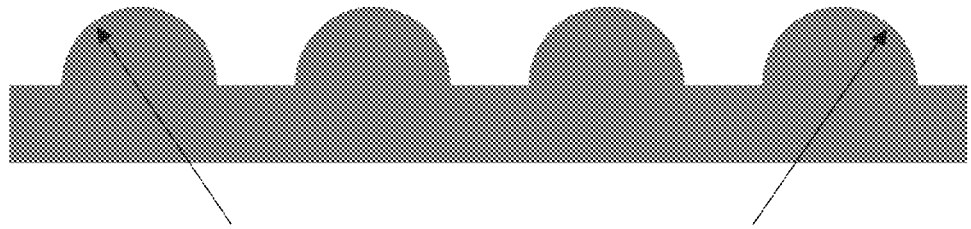
Figure 1:
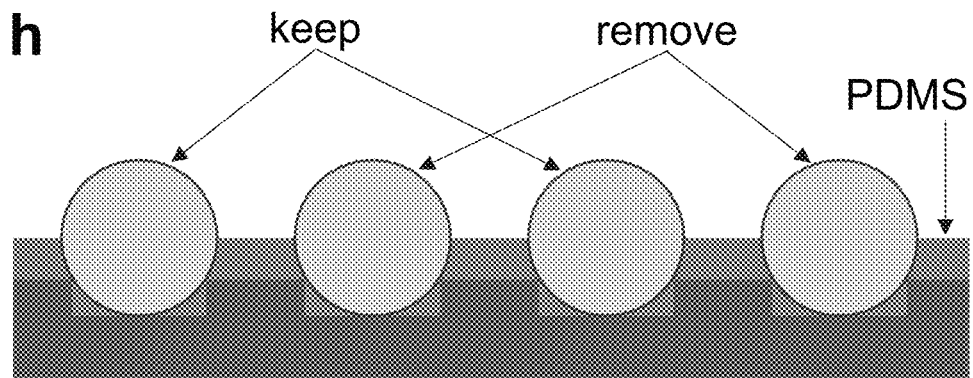
Figure 1:
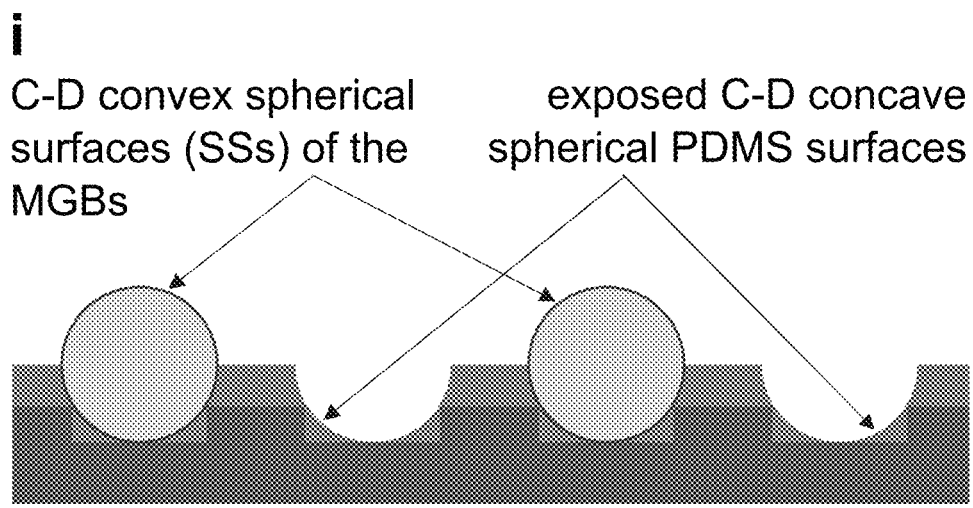
Figure 1:
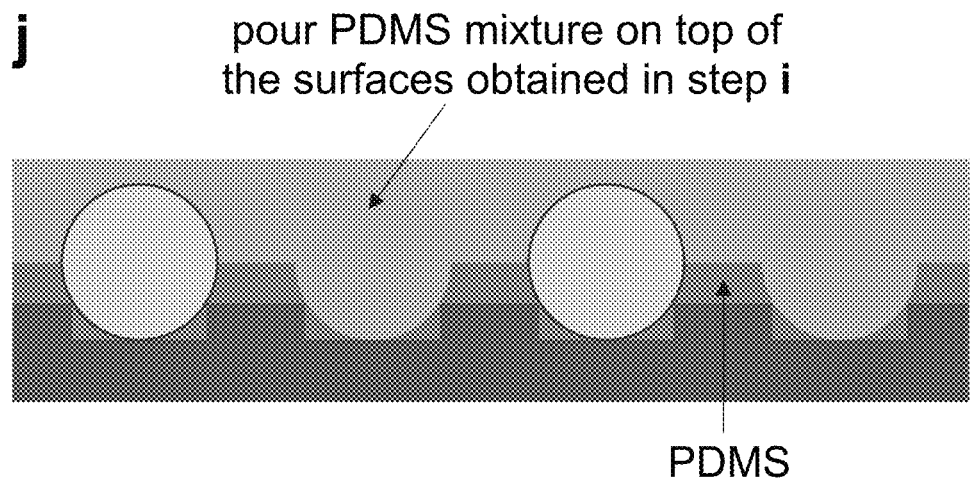
Figure 1:
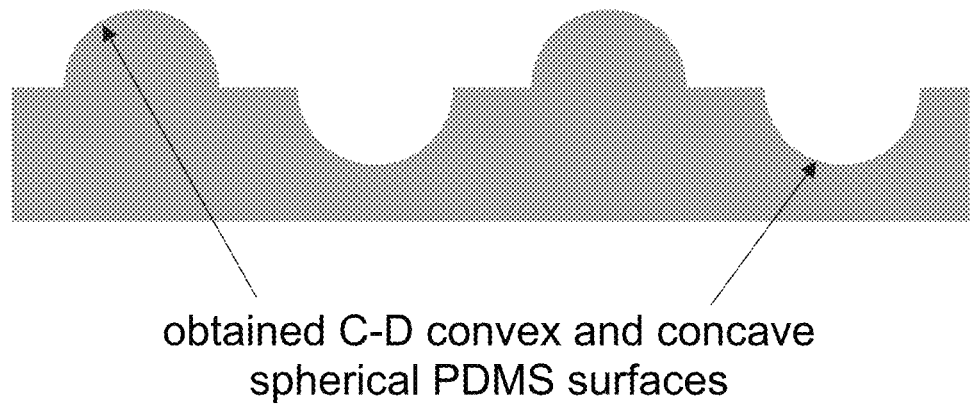

The three aspects of the disclosure are described below. It should be understood that numerous specific backgrounds, details, relationships, methods, discussions, and applications are set forth to provide a full understanding of the disclosure. One having ordinary skill in the relevant art will, therefore, readily recognize that the disclosure can be practiced without one or more of the specific details or practiced with other methods, protocols, and reagents. The present disclosure is not limited by the illustrated ordering of acts or events, as some acts may occur in different orders and/or concurrently with other acts or events. Furthermore, not all illustrated acts, steps, or events are required to implement a methodology in accordance with the present disclosure. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

The terminology used herein is for the purpose of describing particular embodiments only and is not intended to be limiting of the disclosure. As used herein, the articles "a", "an" and "the" should be understood to include plural reference unless the context clearly indicates otherwise.

The phrase "and/or," as used herein, should be understood to mean "either or both" of the elements so conjoined, i.e., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

The term "surface curvature of a substrate" is used interchangeably with the term "substrate curvature."

The First Aspect of the Disclosure

In the first aspect, the disclosure provides a method of fabricating C-D or S-D concave and convex surfaces for use in cell and tissue culturing and in other surface and interface applications. In a specific aspect of this first aspect, the disclosure provides a method of fabricating C-D or S-D concave and convex PDMS surfaces for use in cell and tissue culturing and in other surface and interface applications. In a more specific aspect of this first aspect, the disclosure provides a method of fabricating C-D or S-D concave and convex spherical PDMS surfaces for use in cell and tissue culturing and in other surface and interface applications.

MGB Embedded PDMS Substrates—

By using the same idea of making MGB embedded PA gels, C-D MGB embedded PDMS substrates for cell culturing may also be made through utilizing the polymerization process of forming PDMS microstructures to immobilize the MGBs (see FIGS. 1a and b). Because of the much larger Young's moduli of PDMS materials compared with those of PA gels, PDMS substrates are much more rigid and their geometrical sizes are much less temperature-sensitive than those of PA gels, and then embedding and holding a MGB on the surface of a PDMS substrate should be much easier than on the surface of a PA gel, and an embedded MGB should be much less likely to roll on and detach from the surface of a PDMS substrate than to roll on and detach from the surface of a PA gel. Therefore, overall to make and use MGB embedded PDMS substrates should be much easier than to make and use MGB embedded PA gels for cell culturing (as discussed in the online supporting information of Ref. (Lee and Yang, 2017), it is very challenging to make and use MGB embedded PA gels for cell culturing, majorly due to the significant rolling and detaching of the embedded MGBs on and from the surfaces of the PA gels during the entire experimental process).

Also, the microstructures to be embedded on the surfaces of the PDMS substrates do not have to be MGBs, and depending on the desired cellular studies, any microstructures with well-defined surface shapes may be embedded and the sizes of the embedded microstructures do not have to be the same in a single cell culturing substrate. For examples, micro glass cylinders may be embedded on the surfaces of the PDMS to make substrates to study the cellular responses to cylindrical substrates with various diameters; Micro oval bodies may be embedded to study the cellular responses to surfaces with varying curvatures; Square-shaped and rectangular-shaped micro bodies/particles may be embedded to study the cell mechanosensitivities to locally-rigid or -soft substrate regions, etc. And, the material for the embedded micro balls does not have to be glass, and again depending on the desired studies, the materials for the embedded micro balls or microstructures with any other surface shapes can be anything (e.g., glass, metal, ceramic, silica, silicone, silicon, silicon nitride, PDMS, plastic, and hydrogel, etc.) and the materials for the embedded micro balls or microstructures do not have to be the same in a single cell culturing substrate.

Concave and Convex Spherical PDMS Surfaces—

Again, because the PDMS substrates are much more rigid and their geometrical sizes are much less temperature-sensitive than those of the PA gels, and based on the facts that PDMS is the most commonly used material in soft lithography and the numerous reported PDMS microstructures have been successfully fabricated for cellular studies and other applications by using the casting-onto and peeling-off fabrication process (Park et al., 2009; Fu et al., 2010; Fernandes et al., 2013; Kurabayashi et al., 2013; Soscia et al., 2013; Byun and Kim, 2014; Kim et al., 2018; Lee et al., 2018), besides developing the above-proposed C-D convex MGB embedded PDMS substrates, C-D concave and convex spherical PDMS surfaces may also be developed for cellular studies and their biomedical applications. The exposed concave spherical PDMS surfaces may be obtained by carefully-removing the embedded MGBs from the MGB embedded PDMS substrates (see FIG. 1c). The permanent deformations on the to-be-exposed concave SS of a PDMS substrate induced by the possible significant pulling and pushing forces between an embedded MGB and the PDMS material during the removing process of this ball, and the shape variations of the exposed concave SS of a PDMS substrate (after the removal of an embedded ball) due to temperature changes, should not be significant. That is, the exposed concave SS of a PDMS substrate may not have the above-mentioned concern for the exposed concave SS of a PA gel (due to the removal of an embedded ball) on the two possible sources of significant shape deviation with respect to an exact replica of the shape of the convex SS of the corresponding removed ball. Then we may treat the exposed concave SS of a PDMS substrate as a curvature-defined SS with the radius of the corresponding removed ball.

The exposed concave spherical PDMS surfaces may also be obtained by taking advantage of the convex SSs of the exposed parts of the embedded MGBs of the MGB embedded PDMS substrates, through using the casting-onto and peeling-off fabrication process (see FIGS. 1d and e). That is, the mixture of the precursor and crosslinker of PDMS at an appropriate ratio is poured onto a MGB embedded PDMS substrate, and after curing, the upper newly-solidified PDMS layer is carefully peeled off from the bottom original MGB embedded PDMS substrate. The peeled off upper PDMS layer is a fabricated PDMS substrate having exposed concave SSs. If we take advantage of the concave SSs of this fabricated PDMS substrate by using the casting-onto and peeling-off fabrication process again, a PDMS substrate having convex SSs may be obtained (see FIG. if and g). Note that, this newly-obtained PDMS substrate having convex SSs is entirely made of the PDMS material, in contrast with the MGB embedded PDMS substrates where the convex SSs are from the embedded MGBs. Therefore, by using the C-D MGB embedded PDMS substrates, both concave and convex spherical PDMS surfaces may be fabricated. Moreover, by removing some of the embedded MGBs from a MGB embedded PDMS substrate and keeping the rest of the embedded MGBs, we can have both concave and convex SSs presented on a single substrate (see FIGS. 1h and i). By using the casting-onto and peeling-off fabrication process to this substrate having both the concave PDMS SSs and convex MGB SSs, we may obtain a PDMS substrate having both concave and convex SSs which are made of the (same) PDMS material (see FIGS. 1j and k), and again we may treat these obtained concave and convex spherical PDMS surfaces as C-D SSs with the radii of the corresponding original generating MGB. A PDMS substrate having C-D concave and/or convex SSs may also be further fabricated to realize some other desired non-planar substrates with well-defined 3D surface shapes.

Substrate Curvature Modulates Cell Contractility—

It is well-known that, the mean cell spread area and the mean cell contractility (i.e., the mean cellular traction forces) of the hMSCs growing on a PA gel decrease with the decrease of the stiffness of the PA gel (Engler et al., 2006). The mean cell spread area and the mean cell contractility of the hMSCs plated on the PDMS micropost arrays also decrease with the decrease of the substrate rigidity (Fu et al., 2010). In our experiments, as summarized in the above Section of "Cell Experimental Findings—" in "Background", we found that, overall the mean cell spread area of the hMSCs growing on the MGBs (embedded on the surfaces of the PA gels), decreased with the decrease of the substrate ball diameter. But, unlike the cases of cells growing on the PA gels and PDMS micropost arrays where the cellular traction forces acting on the surfaces of the PA gels and on the tops of the microposts are measured by the displacements of the beads embedded in the PA gels and by the deflections of the microposts, respectively, here the cellular traction forces acting on the surfaces of the MGBs cannot be measured. Nevertheless, according to the theoretical analysis presented in Ref. (Sanz-Herrera et al., 2009), cell contractility decreases with the increase of substrate curvature, and then overall the mean contractility of the cells growing on the MGBs should decrease with the decrease of the substrate ball diameter. Therefore, instead of the substrate matrix elasticity and substrate rigidity that the PA gels and PDMS micropost arrays tune respectively to modulate cell contractility, the MGBs here vary the surface curvature to modulate cell contractility while the modulus of elasticity of the material and the rigidity of a substrate glass ball are infinitely high with respect to those of a cell. That is, independent from substrate matrix elasticity and substrate rigidity, substrate curvature presents another substrate mechanical parameter to modulate cell contractility, and the decreased cell contractility can be realized on stiff and/or rigid substrates by purely increasing the surface curvature of the stiff and/or rigid substrates.

Arrays of the Convex and Concave SSs—

The fact that, substrate curvature can modulate cell contractility independently from substrate matrix elasticity and substrate rigidity, may motivate researchers to design and fabricate new curved substrates with well-defined surface shapes and design and conduct new related experiments to study the possible detailed underlying biophysical mechanisms and biomolecular signaling pathways for the observed adhesion, spreading, migration, and division responses of stem cells on curved surfaces and for the observed differentiation responses of stem cells to the mechanical factors including substrate geometries, substrate matrix elasticity, and substrate rigidity. More specifically, by using the well-established and widely-used micro-patterning technologies (Madou, 2011; Liu, 2012), MGBs of the desired diameter may be embedded on the surface of a PDMS substrate in arrays, as illustrated in FIGS. 1a and b. Then as done in the above Section of "Concave and Convex Spherical PDMS Surfaces—" in "The First Aspect of the Disclosure", a PDMS substrate with the arrays of the C-D concave SSs of the corresponding desired radius may be obtained by carefully-removing the arrays of the embedded MGBs from the obtained PDMS substrate with the arrays of the embedded MGBs (see FIG. 1c), or by using the casting-onto and peeling-off fabrication process on the entire surface of the obtained PDMS substrate with the arrays of the embedded MGBs (see FIGS. 1d and e). A PDMS substrate with the arrays of the C-D convex spherical PDMS surfaces of this same radius may be obtained by using the casting-onto and peeling-off fabrication process again on the entire surface of the obtained PDMS substrate with the arrays of the C-D concave SSs (see FIG. if and g). To record the information on which MGB generated which concave SS and which concave SS generated which convex SS, and for the possible future alignment needs between the concave SSs and the corresponding generating MGBs or between the convex SSs and the corresponding generating concave SSs of these obtained PDMS substrates, multiple identification and alignment markers need to be made on these PDMS substrates in the fabrication process to precisely memorize the relative orientations and positions of these PDMS substrates when the concave SSs and convex SSs were generated.

The first aspect of the disclosure provides the following non-limiting embodiments:

Embodiment 1. A method of fabricating curvature-defined (C-D) or shape-defined (S-D) concave and convex surfaces for use in cell and tissue culturing and in other surface and interface applications, comprising:

(1) embedding rigid C-D or S-D convex microstructures on a solidified first material layer of a sufficient rigidity through the polymerization or solidification process to form this solidified first material layer of a sufficient rigidity, and then the exposed C-D or S-D concave surfaces being obtained by carefully-removing these embedded rigid C-D or S-D convex microstructures from this solidified first material layer of a sufficient rigidity, wherein the curvatures of the obtained exposed C-D or S-D concave surfaces are same to those of the C-D or S-D convex surfaces of the corresponding removed rigid convex microstructures that generated these exposed C-D or S-D concave surfaces, and wherein, the sufficient rigidity of a solidified material layer means that (same below), this solidified material layer is rigid enough or the elastic moduli of this solidified material layer is large enough so that, the permanent deformations on the to-be-exposed concave surface of this solidified material layer induced by the possible significant pulling and pushing forces between an embedded rigid C-D or S-D convex microstructure and this solidified material layer during the removing process of this embedded rigid convex microstructure, and the shape variations of the exposed concave surface of this solidified material layer (after the removal of an embedded rigid C-D or S-D convex microstructure) due to the temperature changes from room temperature to cell and tissue culturing temperature, should not be significant, and then: the shape deviation of the exposed concave surface of this solidified material layer due to the removal of an embedded rigid C-D or S-D convex microstructure with respect to an exact replica of the shape of the C-D or S-D convex surface of the corresponding removed rigid convex microstructure should not be significant, or the obtained exposed concave surface of this solidified material layer may be treated as a C-D or S-D concave surface, and the curvatures of this obtained exposed C-D or S-D concave surface are same to those of the C-D or S-D convex surface of the corresponding removed rigid convex microstructure that generated this exposed C-D or S-D concave surface;

(2) the exposed C-D or S-D concave surfaces being obtained by taking advantage of the C-D or S-D convex surfaces of the exposed parts of the embedded rigid convex microstructures on the above first material layer of a sufficient rigidity in (1) through using the casting-onto and peeling-off fabrication process, i.e., the mixture of the precursor and crosslinker at an appropriate ratio of a second material layer of a sufficient rigidity being poured onto the first material layer of a sufficient rigidity embedded with the rigid convex microstructures, and after curing, the upper newly-solidified second material layer of a sufficient rigidity being carefully peeled off from the bottom first material layer, wherein the peeled-off upper solidified second material layer of a sufficient rigidity is a fabricated substrate having C-D or S-D concave surfaces, wherein the curvatures of the C-D or S-D concave surfaces of the peeled-off upper second material layer are same to those of the C-D or S-D convex surfaces of the corresponding rigid convex microstructures (embedded on the first material layer) that generated these C-D or S-D concave surfaces;

(3) by using the casting-onto and peeling-off fabrication process onto the above-obtained C-D or S-D concave surfaces in (1) or (2), a substrate of a sufficient rigidity having C-D or S-D convex surfaces being obtained, wherein the curvatures of the C-D or S-D convex surfaces of this newly-obtained substrate are same to those of the corresponding C-D or S-D concave surfaces that generated these C-D or S-D convex surfaces, and wherein this newly-obtained substrate having C-D or S-D convex surfaces is entirely made of a same material, which is in contrast with the above first material layer in (1) embedded with rigid C-D or S-D convex microstructures where the C-D or S-D convex surfaces are from the embedded rigid C-D or S-D convex microstructures;

(4) by carefully-removing some of the embedded rigid C-D or S-D convex microstructures from the above first material layer of a sufficient rigidity in (1) embedded with rigid C-D or S-D convex microstructures and keeping the rest of the embedded rigid C-D or S-D convex microstructures, a single substrate of a sufficient rigidity having both C-D or S-D concave and convex surfaces being obtained, wherein the curvatures of the obtained exposed C-D or S-D concave surfaces are same to those of the C-D or S-D convex surfaces of the corresponding removed rigid convex microstructures that generated these exposed C-D or S-D concave surfaces, and wherein the C-D or S-D convex surfaces of this single substrate having both C-D or S-D concave and convex surfaces are from the remaining embedded rigid C-D or S-D convex microstructures;

(5) by using the casting-onto and peeling-off fabrication process onto the above-obtained substrate of a sufficient rigidity having both C-D or S-D concave and convex surfaces in (4), a substrate of a sufficient rigidity having both C-D or S-D convex and concave surfaces being obtained, wherein this newly-obtained substrate of a sufficient rigidity having both C-D or S-D convex and concave surfaces is entirely made of a same material, which is in contrast with the above-obtained substrate having both C-D or S-D concave and convex surfaces in (4) where the C-D or S-D convex surfaces are from the embedded rigid C-D or S-D convex microstructures, and wherein the curvatures of the C-D or S-D convex surfaces of this newly-obtained substrate having both C-D or S-D convex and concave surfaces are same to those of the corresponding C-D or S-D concave surfaces, exposed on the first material layer obtained in (4), which generated these C-D or S-D convex surfaces, and the curvatures of the C-D or S-D concave surfaces of this newly-obtained substrate having both C-D or S-D convex and concave surfaces are same to those of the C-D or S-D convex surfaces of the corresponding rigid C-D or S-D convex microstructures, remained embedded on the first material layer in (4), which generated these C-D or S-D concave surfaces;

(6) by repeatedly using the casting-onto and peeling-off fabrication process onto the above-obtained substrate having C-D or S-D convex surfaces in (3), and onto the above-obtained substrate having both C-D or S-D convex and concave surfaces in (5), the shapes and curvatures of the original C-D or S-D convex and concave surfaces being copied to obtain new substrates of a sufficient rigidity having C-D or S-D concave surfaces, having C-D or S-D convex surfaces, and having both C-D or S-D concave and convex surfaces that are entirely made of same materials, as the situations described in (2), (3), and (5).

Embodiment 2. The method of Embodiment 1, wherein the shapes and/or curvatures, and sizes of the rigid C-D or S-D convex microstructures embedded on the solidified first material layer of a sufficient rigidity can be same or different. Then, the shapes and/or curvatures, and sizes of the final fabricated C-D or S-D concave and convex surfaces can be same or different.

Embodiment 3. The method of Embodiment 1, wherein the sizes of the rigid C-D or S-D convex microstructures embedded on the solidified first material layer of a sufficient rigidity can range from about one nanometer to about several centimeters or above. Then, the sizes of the final fabricated C-D or S-D concave and convex surfaces can range from about one nanometer to about several centimeters or above.

Embodiment 4. The method of Embodiment 1, wherein the materials of the rigid C-D or S-D convex microstructures embedded on the solidified first material layer of a sufficient rigidity can be same or different.

Embodiment 5. The method of Embodiment 1, wherein the materials of the rigid C-D or S-D convex microstructures embedded on the solidified first material layer of a sufficient rigidity comprise glass, metal, ceramic, silica, silicone, silicon, silicon nitride, PDMS, and plastic.

Embodiment 6. The method of Embodiment 1, wherein the embedded rigid C-D or S-D convex microstructures are rigid C-D or S-D convex spherical microstructures.

Embodiment 7. The method of Embodiment 6, wherein the diameters of the embedded rigid C-D or S-D convex spherical microstructures can be same or different.

Embodiment 8. The method of Embodiment 6, wherein the embedded rigid C-D or S-D convex spherical microstructures comprise diameters of between about one nanometer and about several centimeters or above.

Embodiment 9. The method of Embodiment 1, wherein the embedded rigid C-D or S-D convex microstructures are rigid balls.

Embodiment 10. The method of Embodiment 9, wherein the embedded rigid balls are glass balls.

Embodiment 11. The method of Embodiment 1, wherein the rigid C-D or S-D convex microstructures are embedded on the solidified first material layer of a sufficient rigidity as an array or arrays, or as a micro-array or micro-arrays, or as a pattern or patterns, or as a micro-pattern or micro-patterns. Then, the final fabricated C-D or S-D concave and convex surfaces are arranged as the same array or arrays, or as the same micro-array or micro-arrays, or as the same pattern or patterns, or as the same micro-pattern or micro-patterns.

Embodiment 12. The method of Embodiment 1, wherein the embedded rigid C-D or S-D convex microstructures are selected from the group consisting of rigid C-D or S-D convex oval microstructures, rigid C-D or S-D convex elliptical microstructures, rigid C-D or S-D convex cylindrical microstructures, rigid C-D or S-D convex circular microstructures, rigid C-D or S-D convex square microstructures, rigid C-D or S-D convex rectangular microstructures, and combinations thereof.

Embodiment 13. The method of Embodiment 1, wherein the obtained C-D or S-D concave and convex surfaces comprise a coating selected from the group consisting of a cell adhesive, a cell adhesion-promotor, a cell repellent, or a combination thereof.

Embodiment 14. A method of fabricating C-D or S-D concave and convex PDMS surfaces for use in cell and tissue culturing and in other surface and interface applications, comprising:

(1) embedding rigid C-D or S-D convex microstructures on a solidified first PDMS material layer through the polymerization or solidification process of the mixture of the precursor and crosslinker of PDMS at an appropriate ratio, and then the exposed C-D or S-D concave PDMS surfaces being obtained by carefully-removing these embedded rigid C-D or S-D convex microstructures from this solidified first PDMS material layer, wherein the curvatures of the obtained exposed C-D or S-D concave PDMS surfaces are same to those of the C-D or S-D convex surfaces of the corresponding removed rigid convex microstructures that generated these exposed C-D or S-D concave PDMS surfaces;

(2) the exposed C-D or S-D concave PDMS surfaces being obtained by taking advantage of the C-D or S-D convex surfaces of the exposed parts of the embedded rigid convex microstructures on the above first PDMS material layer in (1) through using the casting-onto and peeling-off fabrication process, i.e., the mixture of the precursor and crosslinker at an appropriate ratio of a second PDMS material layer being poured onto the first PDMS material layer embedded with the rigid convex microstructures, and after curing, the upper newly-solidified second PDMS material layer being carefully peeled off from the bottom first PDMS material layer, wherein the peeled-off upper solidified second PDMS material layer is a fabricated substrate having C-D or S-D concave PDMS surfaces, wherein the curvatures of the C-D or S-D concave PDMS surfaces of the peeled-off upper second PDMS material layer are same to those of the C-D or S-D convex surfaces of the corresponding rigid convex microstructures (embedded on the first PDMS material layer) that generated these C-D or S-D concave PDMS surfaces;

(3) by using the casting-onto and peeling-off fabrication process onto the above-obtained C-D or S-D concave PDMS surfaces in (1) or (2), a PDMS substrate having C-D or S-D convex PDMS surfaces being obtained, wherein the curvatures of the C-D or S-D convex PDMS surfaces of this newly-obtained PDMS substrate are same to those of the corresponding C-D or S-D concave PDMS surfaces that generated these C-D or S-D convex PDMS surfaces, and wherein this newly-obtained PDMS substrate having C-D or S-D convex PDMS surfaces is entirely made of a same PDMS material, which is in contrast with the above first PDMS material layer in (1) embedded with rigid C-D or S-D convex microstructures where the C-D or S-D convex surfaces are from the embedded rigid C-D or S-D convex microstructures;

(4) by carefully-removing some of the embedded rigid C-D or S-D convex microstructures from the above first PDMS material layer in (1) embedded with rigid C-D or S-D convex microstructures and keeping the rest of the embedded rigid C-D or S-D convex microstructures, a single substrate having both C-D or S-D concave and convex surfaces being obtained, wherein the curvatures of the obtained exposed C-D or S-D concave PDMS surfaces are same to those of the C-D or S-D convex surfaces of the corresponding removed rigid convex microstructures that generated these exposed C-D or S-D concave PDMS surfaces, and wherein the C-D or S-D convex surfaces of this single substrate having both C-D or S-D concave and convex surfaces are from the remaining embedded rigid C-D or S-D convex microstructures;

(5) by using the casting-onto and peeling-off fabrication process onto the above-obtained substrate having both C-D or S-D concave and convex surfaces in (4), a PDMS substrate having both C-D or S-D convex and concave surfaces being obtained, wherein this newly-obtained PDMS substrate having both C-D or S-D convex and concave surfaces is entirely made of a same PDMS material, which is in contrast with the above-obtained substrate having both C-D or S-D concave and convex surfaces in (4) where the C-D or S-D convex surfaces are from the embedded rigid C-D or S-D convex microstructures, and wherein the curvatures of the C-D or S-D convex PDMS surfaces of this newly-obtained PDMS substrate having both C-D or S-D convex and concave surfaces are same to those of the corresponding C-D or S-D concave PDMS surfaces, exposed on the first PDMS material layer obtained in (4), which generated these C-D or S-D convex PDMS surfaces, and the curvatures of the C-D or S-D concave PDMS surfaces of this newly-obtained PDMS substrate having both C-D or S-D convex and concave surfaces are same to those of the C-D or S-D convex surfaces of the corresponding rigid C-D or S-D convex microstructures, remained embedded on the first PDMS material layer in (4), which generated these C-D or S-D concave PDMS surfaces;

(6) by repeatedly using the casting-onto and peeling-off fabrication process onto the above-obtained PDMS substrate having C-D or S-D convex surfaces in (3), and onto the above-obtained PDMS substrate having both C-D or S-D convex and concave surfaces in (5), the shapes and curvatures of the original C-D or S-D convex and concave surfaces being copied to obtain new PDMS substrates having C-D or S-D concave PDMS surfaces, having C-D or S-D convex PDMS surfaces, and having both C-D or S-D concave and convex PDMS surfaces, as the situations described in (2), (3), and (5).

Embodiment 15. The method of Embodiment 14, wherein the shapes and/or curvatures, and sizes of the rigid C-D or S-D convex microstructures embedded on the solidified first PDMS material layer can be same or different. Then, the shapes and/or curvatures, and sizes of the final fabricated C-D or S-D concave and convex PDMS surfaces can be same or different.

Embodiment 16. The method of Embodiment 14, wherein the sizes of the rigid C-D or S-D convex microstructures embedded on the solidified first PDMS material layer can range from about one nanometer to about several centimeters or above. Then, the sizes of the final fabricated C-D or S-D concave and convex PDMS surfaces can range from about one nanometer to about several centimeters or above.

Embodiment 17. The method of Embodiment 14, wherein the materials of the rigid C-D or S-D convex microstructures embedded on the solidified first PDMS material layer can be same or different.

Embodiment 18. The method of Embodiment 14, wherein the materials of the rigid C-D or S-D convex microstructures embedded on the solidified first PDMS material layer comprise glass, metal, ceramic, silica, silicone, silicon, silicon nitride, PDMS, and plastic.

Embodiment 19. The method of Embodiment 14, wherein the embedded rigid C-D or S-D convex microstructures are rigid C-D or S-D convex spherical microstructures.

Embodiment 20. The method of Embodiment 19, wherein the diameters of the embedded rigid C-D or S-D convex spherical microstructures can be same or different.

Embodiment 21. The method of Embodiment 19, wherein the embedded rigid C-D or S-D convex spherical microstructures comprise diameters of between about one nanometer and about several centimeters or above.

Embodiment 22. The method of Embodiment 14, wherein the embedded rigid C-D or S-D convex microstructures are rigid balls.

Embodiment 23. The method of Embodiment 22, wherein the embedded rigid balls are glass balls.

Embodiment 24. The method of Embodiment 14, wherein the rigid C-D or S-D convex microstructures are embedded on the solidified first PDMS material layer as an array or arrays, or as a micro-array or micro-arrays, or as a pattern or patterns, or as a micro-pattern or micro-patterns. Then, the final fabricated C-D or S-D concave and convex PDMS surfaces are arranged as the same array or arrays, or as the same micro-array or micro-arrays, or as the same pattern or patterns, or as the same micro-pattern or micro-patterns.

Embodiment 25. The method of Embodiment 14, wherein the embedded rigid C-D or S-D convex microstructures are selected from the group consisting of rigid C-D or S-D convex oval microstructures, rigid C-D or S-D convex elliptical microstructures, rigid C-D or S-D convex cylindrical microstructures, rigid C-D or S-D convex circular microstructures, rigid C-D or S-D convex square microstructures, rigid C-D or S-D convex rectangular microstructures, and combinations thereof.

Embodiment 26. The method of Embodiment 14, wherein the obtained C-D or S-D concave and convex PDMS surfaces comprise a coating selected from the group consisting of a cell adhesive, a cell adhesion-promotor, a cell repellent, or a combination thereof.

Embodiment 27. A method of fabricating C-D or S-D concave and convex spherical PDMS surfaces for use in cell and tissue culturing and in other surface and interface applications, comprising:

(1) embedding rigid C-D or S-D convex spherical microstructures on a solidified first PDMS material layer through the polymerization or solidification process of the mixture of the precursor and crosslinker of PDMS at an appropriate ratio, and then the exposed C-D or S-D concave spherical PDMS surfaces being obtained by carefully-removing these embedded rigid C-D or S-D convex spherical microstructures from this solidified first PDMS material layer, wherein the curvatures of the obtained exposed C-D or S-D concave spherical PDMS surfaces are same to those of the C-D or S-D convex spherical surfaces of the corresponding removed rigid convex spherical microstructures that generated these exposed C-D or S-D concave spherical PDMS surfaces;

(2) the exposed C-D or S-D concave spherical PDMS surfaces being obtained by taking advantage of the C-D or S-D convex spherical surfaces of the exposed parts of the embedded rigid convex spherical microstructures on the above first PDMS material layer in (1) through using the casting-onto and peeling-off fabrication process, i.e., the mixture of the precursor and crosslinker at an appropriate ratio of a second PDMS material layer being poured onto the first PDMS material layer embedded with the rigid convex spherical microstructures, and after curing, the upper newly-solidified second PDMS material layer being carefully peeled off from the bottom first PDMS material layer, wherein the peeled-off upper solidified second PDMS material layer is a fabricated substrate having C-D or S-D concave spherical PDMS surfaces, wherein the curvatures of the C-D or S-D concave spherical PDMS surfaces of the peeled-off upper second PDMS material layer are same to those of the C-D or S-D convex spherical surfaces of the corresponding rigid convex spherical microstructures (embedded on the first PDMS material layer) that generated these C-D or S-D concave spherical PDMS surfaces;

(3) by using the casting-onto and peeling-off fabrication process onto the above-obtained C-D or S-D concave spherical PDMS surfaces in (1) or (2), a PDMS substrate having C-D or S-D convex spherical PDMS surfaces being obtained, wherein the curvatures of the C-D or S-D convex spherical PDMS surfaces of this newly-obtained PDMS substrate are same to those of the corresponding C-D or S-D concave spherical PDMS surfaces that generated these C-D or S-D convex spherical PDMS surfaces, and wherein this newly-obtained PDMS substrate having C-D or S-D convex spherical PDMS surfaces is entirely made of a same PDMS material, which is in contrast with the above first PDMS material layer in (1) embedded with rigid C-D or S-D convex spherical microstructures where the C-D or S-D convex spherical surfaces are from the embedded rigid C-D or S-D convex spherical microstructures;

(4) by carefully-removing some of the embedded rigid C-D or S-D convex spherical microstructures from the above first PDMS material layer in (1) embedded with rigid C-D or S-D convex spherical microstructures and keeping the rest of the embedded rigid C-D or S-D convex spherical microstructures, a single substrate having both C-D or S-D concave and convex spherical surfaces being obtained, wherein the curvatures of the obtained exposed C-D or S-D concave spherical PDMS surfaces are same to those of the C-D or S-D convex spherical surfaces of the corresponding removed rigid convex spherical microstructures that generated these exposed C-D or S-D concave spherical PDMS surfaces, and wherein the C-D or S-D convex spherical surfaces of this single substrate having both C-D or S-D concave and convex spherical surfaces are from the remaining embedded rigid C-D or S-D convex spherical microstructures;

(5) by using the casting-onto and peeling-off fabrication process onto the above-obtained substrate having both C-D or S-D concave and convex spherical surfaces in (4), a PDMS substrate having both C-D or S-D convex and concave spherical surfaces being obtained, wherein this newly-obtained PDMS substrate having both C-D or S-D convex and concave spherical surfaces is entirely made of a same PDMS material, which is in contrast with the above-obtained substrate having both C-D or S-D concave and convex spherical surfaces in (4) where the C-D or S-D convex spherical surfaces are from the embedded rigid C-D or S-D convex spherical microstructures, and wherein the curvatures of the C-D or S-D convex spherical PDMS surfaces of this newly-obtained PDMS substrate having both C-D or S-D convex and concave spherical surfaces are same to those of the corresponding C-D or S-D concave spherical PDMS surfaces, exposed on the first PDMS material layer obtained in (4), which generated these C-D or S-D convex spherical PDMS surfaces, and the curvatures of the C-D or S-D concave spherical PDMS surfaces of this newly-obtained PDMS substrate having both C-D or S-D convex and concave spherical surfaces are same to those of the C-D or S-D convex spherical surfaces of the corresponding rigid C-D or S-D convex spherical microstructures, remained embedded on the first PDMS material layer in (4), which generated these C-D or S-D concave spherical PDMS surfaces;

(6) by repeatedly using the casting-onto and peeling-off fabrication process onto the above-obtained PDMS substrate having C-D or S-D convex spherical surfaces in (3), and onto the above-obtained PDMS substrate having both C-D or S-D convex and concave spherical surfaces in (5), the shapes and curvatures of the original C-D or S-D convex and concave spherical surfaces being copied to obtain new PDMS substrates having C-D or S-D concave spherical PDMS surfaces, having C-D or S-D convex spherical PDMS surfaces, and having both C-D or S-D concave and convex spherical PDMS surfaces, as the situations described in (2), (3), and (5).

Embodiment 28. The method of Embodiment 27, wherein the diameters of the rigid C-D or S-D convex spherical microstructures embedded on the solidified first PDMS material layer can be same or different. Then, the diameters of the final fabricated C-D or S-D concave and convex spherical PDMS surfaces can be same or different.

Embodiment 29. The method of Embodiment 27, wherein the diameters of the rigid C-D or S-D convex spherical microstructures embedded on the solidified first PDMS material layer can range from about one nanometer to about several centimeters or above. Then, the sizes of the final fabricated C-D or S-D concave and convex spherical PDMS surfaces can range from about one nanometer to about several centimeters or above.

Embodiment 30. The method of Embodiment 27, wherein the materials of the rigid C-D or S-D convex spherical microstructures embedded on the solidified first PDMS material layer can be same or different.

Embodiment 31. The method of Embodiment 27, wherein the materials of the rigid C-D or S-D convex spherical microstructures embedded on the solidified first PDMS material layer comprise glass, metal, ceramic, silica, silicone, silicon, silicon nitride, PDMS, and plastic.

Embodiment 32. The method of Embodiment 27, wherein the embedded rigid C-D or S-D convex spherical microstructures are rigid balls.

Embodiment 33. The method of Embodiment 32, wherein the embedded rigid balls are glass balls.

Embodiment 34. The method of Embodiment 27, wherein the rigid C-D or S-D convex spherical microstructures are embedded on the solidified first PDMS material layer as an array or arrays, or as a micro-array or micro-arrays, or as a pattern or patterns, or as a micro-pattern or micro-patterns. Then, the final fabricated C-D or S-D concave and convex spherical PDMS surfaces are arranged as the same array or arrays, or as the same micro-array or micro-arrays, or as the same pattern or patterns, or as the same micro-pattern or micro-patterns.

Embodiment 35. The method of Embodiment 27, wherein the obtained C-D or S-D concave and convex spherical PDMS surfaces comprise a coating selected from the group consisting of a cell adhesive, a cell adhesion-promotor, a cell repellent, or a combination thereof.

The Second Aspect of the Disclosure

C-D Convex and Concave Spherical PA Gel Surfaces—

Figure 2:
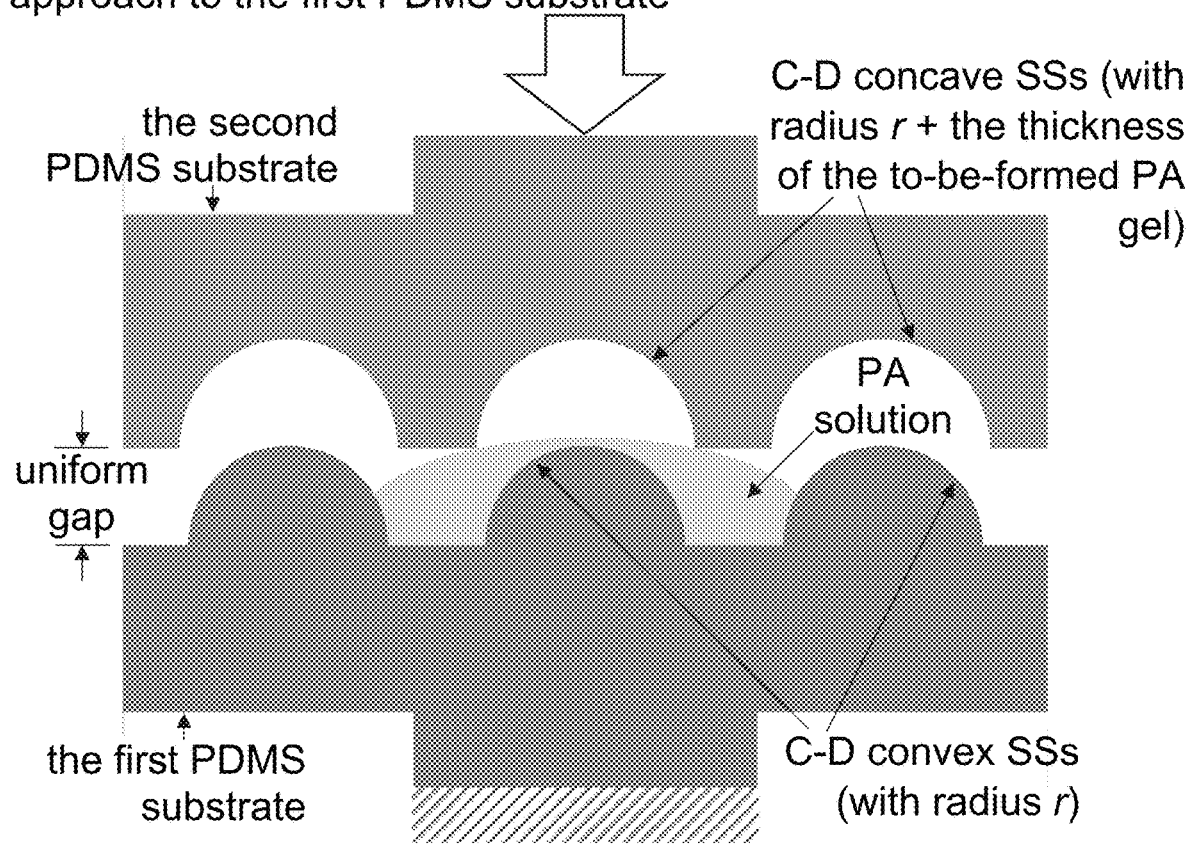
FIG. 2 illustrates the fabrication processes to obtain C-D or S-D convex (a1, a2, and a3) and concave (b1, b2, and b3) spherical polyacrylamide (PA) gel surfaces according to the present invention.
Figure 2:
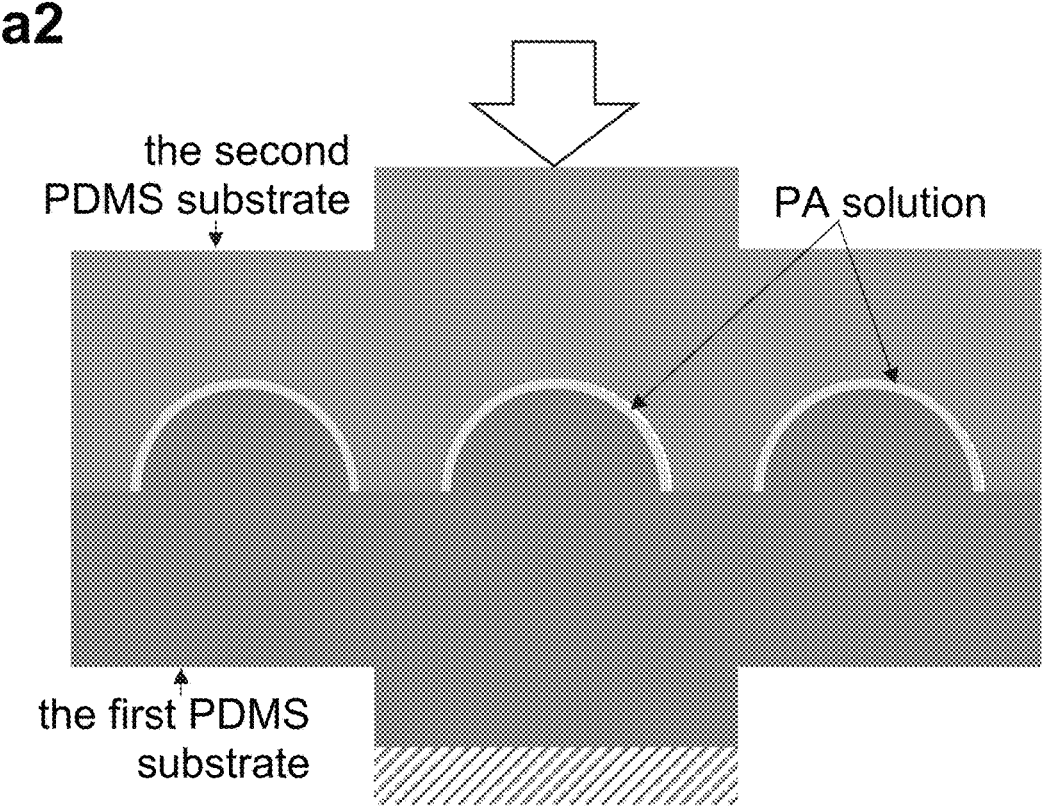
Figure 2:
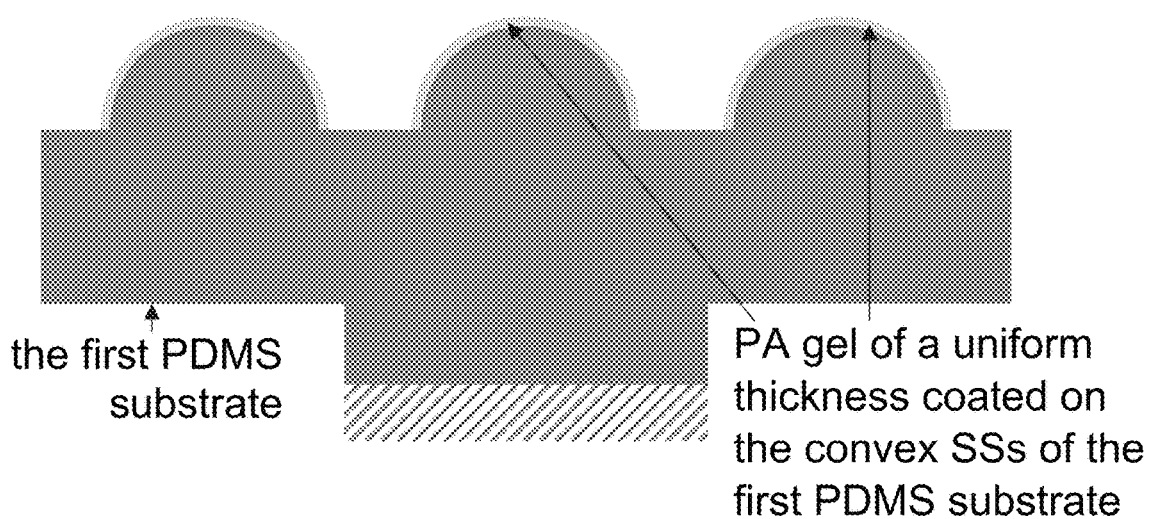
Figure 2:
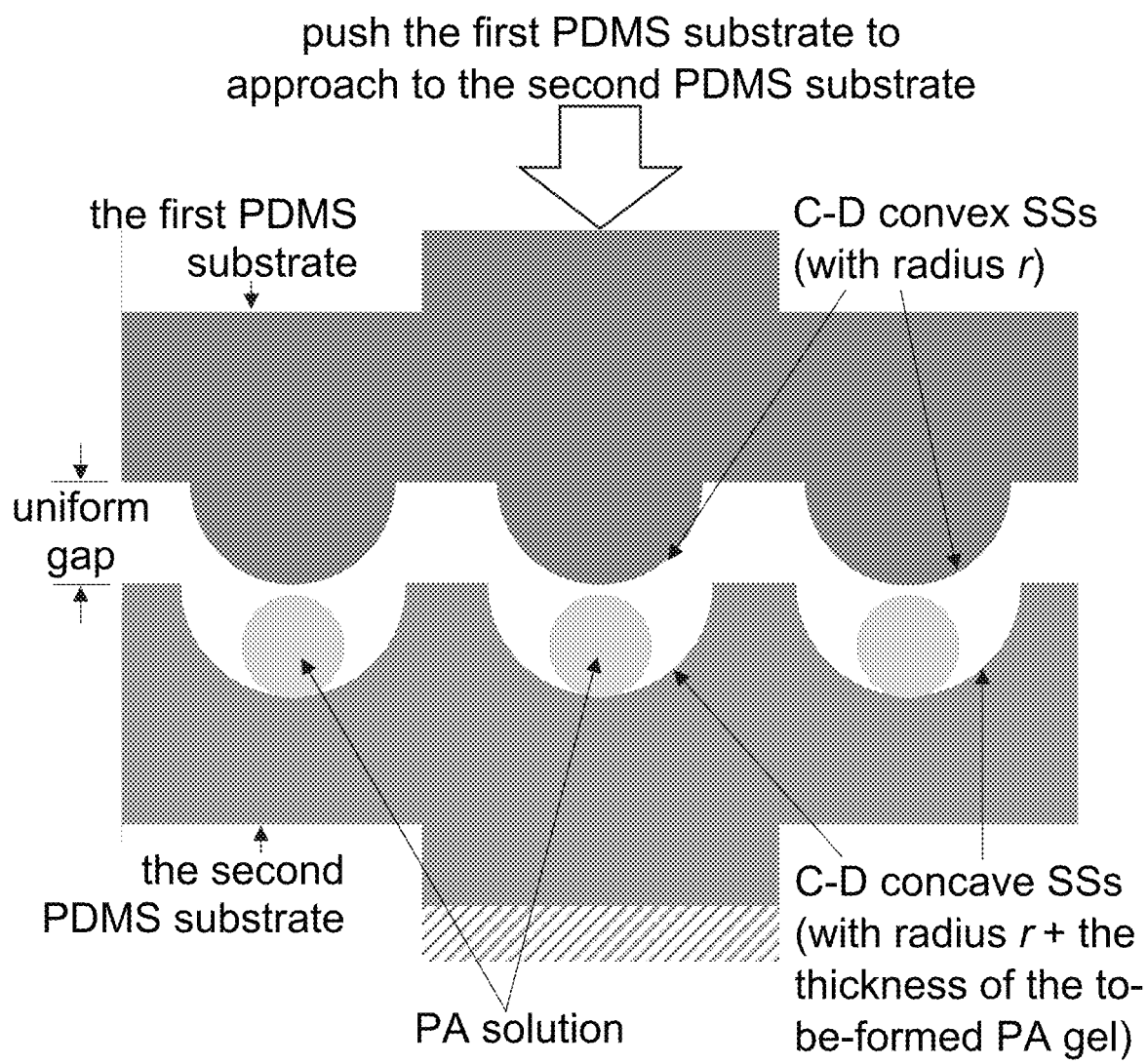
Figure 2:
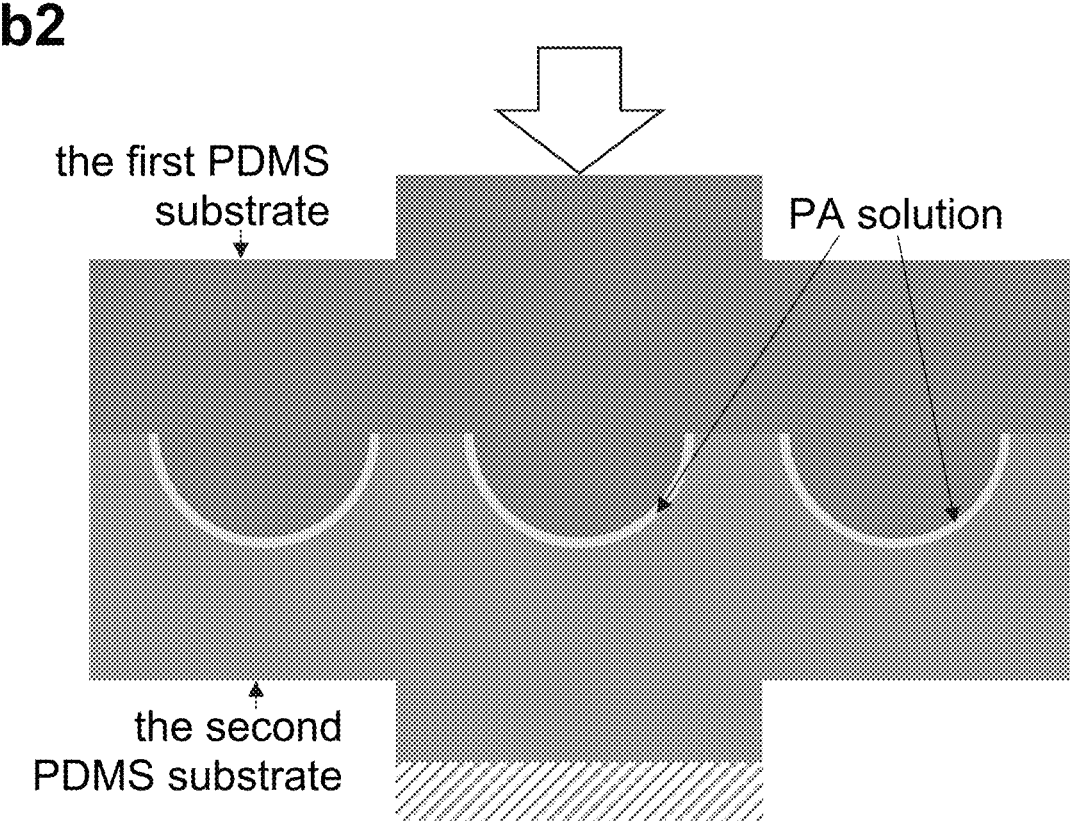
Figure 2:
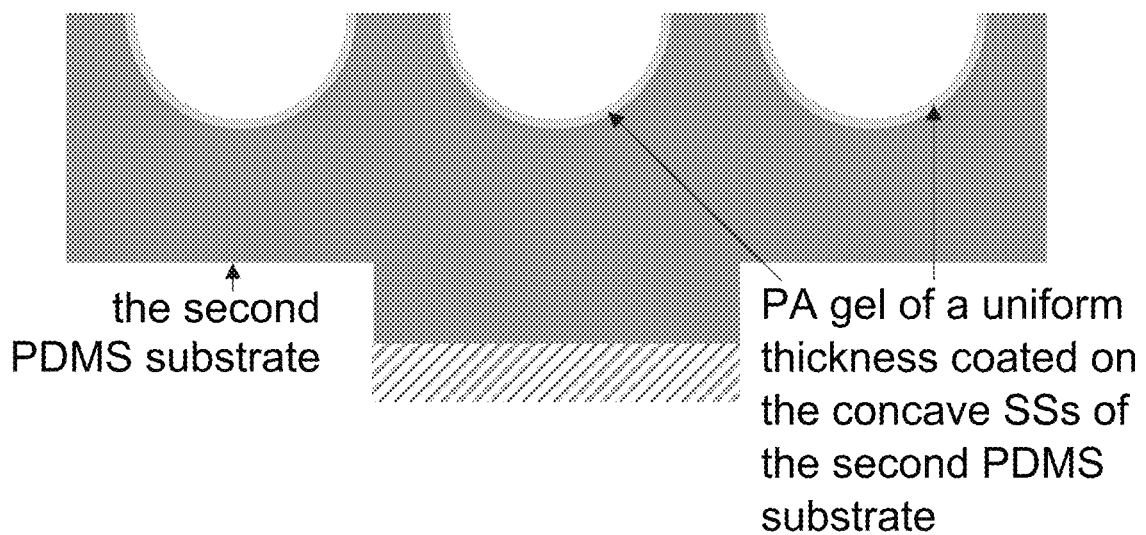

If the surfaces of the embedded MGBs or the C-D convex or concave spherical PDMS surfaces can be coated with a PA gel of a uniform thickness, a substrate with C-D convex or concave spherical PA gel surfaces may be obtained. Compared with the surfaces of the embedded MGBs and the convex and concave spherical PDMS surfaces, besides the curved nature, convex and concave spherical PA gel surfaces can also mimic the stiffness of the native tissues and measure the cellular traction forces, as the case of planar PA gels which are widely-used for cell culturing (as mentioned in the above Section of "Concave Spherical PA Gel Surfaces—" in "Background"). For this purpose, in the following, the PDMS substrate with either the arrays of the embedded MGBs of the desired diameter or the arrays of the C-D convex spherical PDMS surfaces of the desired radius r is called the first PDMS substrate, and the PDMS substrate with the arrays of the C-D concave SSs of the radius r plus the thickness of the to-be-coated PA gel is called the second PDMS substrate (FIG. 2). Depending on the thickness of the PA gel to be coated on the surfaces of the embedded MGBs or on the convex spherical PDMS surfaces of the first PDMS substrate (in the following, the surfaces of the embedded MGBs or the convex spherical PDMS surfaces of the first PDMS substrate are stated in short as the convex SSs of the first PDMS substrate), an appropriate amount of the PA solution with florescent beads will be dropped onto the arrays of the embedded MGBs or the arrays of the convex spherical PDMS surfaces of the first PDMS substrate. Later when this first PDMS substrate is used to culture cells, the displacements of the fluorescent beads in the PA gel coated on the convex SSs of this first PDMS substrate will be used to calculate the cellular traction forces, as is done in the case of planar PA gels for cell culturing.

Before the polymerization of the PA solution, the first and second PDMS substrates will be oriented and precisely aligned with each other so that each of the convex SSs of the first PDMS substrate will face the concave SS of the second PDMS substrate located at the exactly same position to that of the concave SS which this convex SS faced when this concave or convex SS was originally generated. That is, the first and second PDMS substrates here will be oriented and precisely aligned with each other in the way when these two PDMS substrates were originally fabricated which were designed specifically and whose fabrication processes were designed specifically according to the orientation and alignment needs here. The fine adjustment of this alignment will ensure that the centerlines of the concave SSs of the second PDMS substrate are precisely aligned with the centerlines of the corresponding convex SSs of the first PDMS substrate. This high-precision alignment between the first and second PDMS substrates may be conducted and may be achieved under an optical microscope with a micro manipulator and with the help of the multiple identification and alignment markers that were specifically made on these PDMS substrates for this purpose. The second PDMS substrate will then be brought to approach to the first PDMS substrate to press the PA solution to uniformly re-distribute the PA solution on the convex SSs of the first PDMS substrate (see FIG. 2a1). The uniform gap between the C-D convex SSs of the first PDMS substrate and the corresponding C-D concave SSs of the second PDMS substrate will ensure that, after the polymerization of the PA solution the thickness of the formed PA gel on top of the convex SSs of the first PDMS substrate is uniform (see FIG. 2a2). After the second PDMS substrate is carefully withdrawn from the first PDMS substrate, the convex SSs of the first PDMS substrate are coated with the PA gel of a uniform thickness (see FIG. 2a3). Then, the first PDMS substrate becomes a substrate with C-D convex spherical PA gel surfaces.

Note that, before the dropping of the PA solution, the entire surface of the first PDMS substrate needs to be coated with the appropriate chemical adhesive agent to ensure the strong adherence of the to-be-formed PA gel to the convex SSs of the first PDMS substrate, and the entire surface of the second PDMS substrate needs to be coated with the appropriate chemical repellent agent to ensure the second PDMS substrate can be easily withdrawn or detached from the to-be-exposed convex spherical PA gel surfaces without damaging these to-be-exposed PA gel surfaces. As summarized in the above Section of "Cell Experimental Findings—" in "Background"), we found that, among the used diameters, the minimum diameter of a glass ball on which an hMSC can attach and spread was 500 µm. It is reported that hMSCs increasingly respond to the rigidity of an underlying 'hidden' surface starting at about 10-20 µm PA gel thickness with a characteristic tactile length of less than about 5 µm (Buxboim et al., 2010). Then the thickness of the PA gel to be coated on the convex SSs of the first PDMS substrate for the desired cellular studies may be chosen as small as 20-30 µm. Due to the relatively very small thickness of the coated PA gel with respect to the diameter of the embedded MGBs or the radius of the convex spherical PDMS surfaces, and due to the uniform thickness of the PA gel coated on the convex SSs of the first PDMS substrate, unlike the situation of obtaining exposed concave spherical PA gel surfaces by carefully-removing the embedded MGBs from the MGB embedded PA gels (discussed in the above Section of "Concave Spherical PA Gel Surfaces—" in "Background"), here the possible pulling and pushing forces between the to-be-exposed convex spherical PA gel surfaces of the first PDMS substrate and the concave SSs of the second PDMS substrate during the withdrawing process of the second PDMS substrate may not be significant and then the permanent deformations on the to-be-exposed convex spherical PA gel surfaces induced by these possible pulling and pushing forces may not be significant, and the shape variations of the exposed convex spherical PA gel surfaces due to temperature changes may also not be significant. Therefore, the final convex spherical PA gel surfaces of the first PDMS substrate, formed by coating the PA gel of a uniform thickness onto the surfaces of the embedded MGBs or onto the C-D convex spherical PDMS surfaces of the first PDMS substrate by using the above method (see the last two paragraphs), may be treated as C-D convex SSs.

With respect to an exact C-D convex SS of a desired radius, the shape accuracy of these formed convex SSs of the PA gel will be highly dependent on the precision of the alignment between the first and second PDMS substrates when the second PDMS substrate presses the PA solution to re-distribute the PA solution on the convex SSs of the first PDMS substrate, and highly dependent on the thickness of the remaining PA solution between the contacting flat parts of the first and second PDMS substrates. A complete squeezing-out of the PA solution between the flat parts of the first and second PDMS substrates is impossible, but a lot of practice may help establish a strategy to minimize the thickness of the remaining PA solution between these contacting flat parts, and to uniformly re-distribute the PA solution on the convex SSs of the first PDMS substrate. The high-precision alignment between the first and second PDMS substrates will ensure that, the gap between the C-D convex SSs of the first PDMS substrate and the corresponding C-D concave SSs of the second PDMS substrate is uniform, and this uniform gap will ensure the thickness of the PA gel formed in the gap and coated on top of the convex SSs of the first PDMS substrate is uniform. The great success of the high-precision alignment between a mask and a silicon wafer in the widely-used traditional micro-patterning technology—photolithography (Madou, 2011; Liu, 2012) shows that the high-precision alignment between the first and second PDMS substrates required here will be achievable, and then the high shape accuracy of the above-formed convex spherical PA gel surfaces of the first PDMS substrate may also be achievable.

C-D concave spherical PA gel surfaces may also be obtained by using the same above method if the roles of the above first and second PDMS substrates are exchanged. That is, the entire surface of the above first PDMS substrate, with the arrays of the embedded MGBs or the arrays of the C-D convex spherical PDMS surfaces of the desired radius r, needs to be coated with the appropriate chemical repellent agent to ensure the first PDMS substrate can be easily withdrawn or detached from the to-be-exposed concave spherical PA gel surfaces without damaging these to-be-exposed PA gel surfaces, and the entire surface of the above second PDMS substrate, with the arrays of the C-D concave SSs of the radius r plus the thickness of the to-be-coated PA gel, needs to be coated with the appropriate chemical adhesive agent to ensure the strong adherence of the to-be-formed PA gel to the concave SSs of the second PDMS substrate. An appropriate amount of the PA solution with florescent beads will be dropped onto the arrays of the concave SSs of the second PDMS substrate. The first PDMS substrate will then be brought to approach to the second PDMS substrate to press the PA solution to uniformly re-distribute the PA solution on the concave SSs of the second PDMS substrate (see FIG. 2$b$1 and b2). After the polymerization of the PA solution and after the first PDMS substrate is carefully withdrawn from the second PDMS substrate, the concave SSs of the second PDMS substrate are coated with the PA gel of a uniform thickness (see FIG. 2$b$3). Then, the second PDMS substrate is now a substrate with concave spherical PA gel surfaces, and due to the above same reasons, these concave spherical PA gel surfaces may also be treated as C-D concave SSs.

Combined Effects of Substrate Curvature and Matrix Elasticity on Cellular Traction Forces—

The above C-D convex and concave spherical PA gel surfaces combine the C-D culturing technology with the PA gel technology, which can be used to study the combined effects of substrate curvature and matrix elasticity on cellular behaviors and can be especially used to study the effects of substrate curvatures on cellular traction forces. To measure the traction forces of cells growing on curved surfaces, as were done in Ref. (Franck et al., 2011; Soine et al., 2016), the confocal laser scanning microscopy will be used to image the cells growing on these convex and concave spherical PA gel surfaces and to image the positions of the fluorescent beads embedded in the PA gel in 3D, an appropriate algorithm will be adopted or developed to track the 3D displacements of the fluorescent beads, and then the 3D cellular traction force field will be obtained by solving an inverse elasticity problem. If the radius of a convex or concave spherical PA gel surface is large enough compared with the geometrical sizes of a cell growing on this SS and if this cell is also growing approximately in the center region of this SS, this SS is virtually flat with respect to the sizes of this cell, and we may then approximately treat this spherical PA gel surface as a flat PA gel surface which is the projection of this spherical PA gel surface onto the horizontal plane. In this case, the 3D cellular traction force field on this spherical PA gel surface may be simplified as the 2D cellular traction force field on the approximated flat PA gel surface which can be obtained by using the existing method for obtaining the 2D cellular traction force field on a flat PA gel surface (Dembo and Wang, 1999; Jacobs et al., 2012). If the obtained 2D cellular traction force field is regarded as the in-plane components of the real 3D cellular traction force field on this spherical PA gel surface, the errors of this obtained in-plane components of the real 3D cellular traction force field induced by this approximately treating this spherical PA gel surface as the flat PA gel surface should not be significant.

As summarized in the above Section of "Cell Experimental Findings—" in "Background", we found that, the attachment of an hMSC is much more sensitive to the large surface curvatures of the small substrate glass balls than that of a fibroblast, and the spreading morphology of an hMSC is much more sensitive to the small surface curvatures of the large substrate glass balls than that of a fibroblast. Then it will be interesting to investigate these corresponding mechanosensitivities of an hMSC and a fibroblast cultured on the above convex spherical PA gel surfaces.

Substrate Curvature Effects of Focal Adhesion Strength and Contractile Actomyosin Apparatus—

The experiments to systematically study the time-lapse curvature-dependent responses of the adhesion, spreading, migration, and division behaviors of the stem cells cultured on the above PDMS substrates with C-D convex and concave SSs (including the MGB embedded PDMS substrates, PDMS substrates with convex spherical PDMS surfaces, PDMS substrates with concave SSs, and PDMS substrates with convex and concave spherical PA gel surfaces) need to be designed and conducted. In these studies, for the three cellular components that determine the cell contractility, namely the focal adhesions, stress fibers, and contractile actomyosin apparatus, the dependences of the size, strength, number, and distribution of the focal adhesions on surface curvature may be observed or deduced, the dependences of the structure, distribution, prestress, and tensional and bending mechanics of the stress fibers on surface curvature may be observed or deduced, and the dependence of the contractile force generated by the actomyosin apparatus on surface curvature may be deduced (Sanz-Herrera et al., 2009). Atomic force microscopy (AFM) indentation and micropipette aspiration may be used to measure the dependences of cell stiffness and cell membrane cortical stiffness on surface curvature, respectively (Engler et al., 2006; Jacobs et al., 2012; Li et al., 2017), and these two measurements may further elucidate the roles of surface curvature in modulating cell contractility. The effects of matrix elasticity on the observed surface curvature-dependent cellular behaviors may be identified.

The quantitative equivalency in the induced reduction of cell contractility between the increase of substrate curvature and the decrease of substrate matrix elasticity and substrate rigidity, i.e., the quantitative equivalency between the reduced cell contractility of the cells growing on the C-D SSs (for both the convex and concave situations) with smaller radii and the reduced cell contractility of the cells growing on the softer (flat) PA gels and softer (flat) PDMS micropost arrays, in terms of the induced reductions of mean cell spread area and mean in-plane cellular traction force, may be sought. These studies will also enhance our existing understandings on the detailed matrix elasticity-dependent mechanosensing and mechanotransduction processes of the focal adhesions, stress fibers, and contractile actomyosin apparatus of a cell growing on flat PA gels (Maloney et al., 2008; Cheng et al., 2017; Nicolas, 2017). It was reported that, hMSCs actively "escaped" from the concave microstructures (Park et al., 2009), and hMSCs on the concave surfaces showed an upward stretched cell morphology where a substantial part of the cell body was not attached to the concave surface (Werner et al., 2017). The results of the experiments proposed here will determine the minimum radius of a concave SS on which an hMSC can form focal adhesions and the minimum radius of a concave SS to which an hMSC can entirely attach.

The second aspect of the disclosure provides the following non-limiting embodiments (the numbering of these embodiments is continued from that of the embodiments provided by the first aspect of the disclosure listed in the above):

Embodiment 36. A method of fabricating C-D or S-D convex spherical gel surfaces for use in cell and tissue culturing and in other surface and interface applications, comprising:

a first substrate of a sufficient rigidity having a C-D or S-D convex SS of a desired radius r, coated with an appropriate chemical adhesive agent to ensure the strong adherence of the to-be-formed gel layer to this convex SS, wherein the sufficient rigidity of a substrate means that (same below), this substrate is rigid enough or the elastic moduli of the material of this substrate is large enough compared with the to-be-formed gel layer or its elastic moduli so that the deformations of this substrate are negligibly small compared with those of the to-be-formed gel layer due to a same force;

a second substrate of a sufficient rigidity having a C-D or S-D concave SS of the radius r plus the thickness of the to-be-coated gel layer on the C-D or S-D convex SS of the first substrate, coated with an appropriate chemical repellent agent to ensure this second substrate can be easily withdrawn or detached from the to-be-exposed convex gel surface, coated on the convex SS of the first substrate, without damaging this to-be-exposed convex gel surface;

depending on the thickness of the gel layer to be coated on the C-D or S-D convex SS of the first substrate, an appropriate amount of the gel solution being dropped onto the C-D or S-D convex SS of the first substrate;

the first and second substrates being oriented and precisely aligned with each other so that the centerline of the C-D or S-D concave SS of the second substrate is precisely aligned with the centerline of the C-D or S-D convex SS of the first substrate;

the second substrate then being brought to approach to the first substrate to press the gel solution to uniformly redistribute the gel solution on the C-D or S-D convex SS of the first substrate, wherein, when the center of the C-D or S-D concave SS of the second substrate is on the center of the C-D or S-D convex SS of the first substrate (i.e., when the C-D or S-D concave SS of the second substrate and the C-D or S-D convex SS of the first substrate are concentric), the uniform gap between the C-D or S-D concave SS of the second substrate and the C-D or S-D convex SS of the first substrate will ensure that, after the polymerization of the gel solution the thickness of the formed gel layer on top of the C-D or S-D convex SS of the first substrate is uniform;

and, after the second substrate is carefully withdrawn from the first substrate, the C-D or S-D convex SS of the first substrate being coated with the gel layer of a uniform thickness, wherein the first substrate becomes a substrate with a C-D or S-D convex spherical gel surface.

Embodiment 37. The method of Embodiment 36, wherein, for the precise alignments between the centerline and center of the C-D or S-D concave SS of the second substrate and the centerline and center of the C-D or S-D convex SS of the first substrate, multiple identification and alignment markers were made on the first and second substrates in the fabrication processes of these substrates to precisely memorize the relative orientations and positions of these substrates when the C-D or S-D convex and concave SSs were generated on these substrates.

Embodiment 38. The method of Embodiment 36, wherein the first substrate is a micro ball embedded PDMS substrate wherein the C-D or S-D convex SS of the first substrate is the C-D or S-D convex SS of a ball which is embedded on the surface of a PDMS layer.

Embodiment 39. The method of Embodiment 36, wherein the first substrate is entirely made of PDMS and the C-D or S-D convex SS of the first substrate is a C-D or S-D convex spherical PDMS surface.

Embodiment 40. The method of Embodiment 36, wherein the second substrate is made of PDMS and the C-D or S-D concave SS of the second substrate is a C-D or S-D concave spherical PDMS surface.

Embodiment 41. The method of Embodiment 36, wherein the gel comprises PA gel.

Embodiment 42. The method of Embodiment 36, wherein the diameter of the C-D or S-D convex SS of the first substrate is between about one nanometer and about several centimeters or above.

Embodiment 43. The method of Embodiment 36, wherein the thickness of the gel layer to-be-coated on the C-D or S-D convex SS of the first substrate is between about 1 μm or below and about 100 μm or above.

Embodiment 44. A method of fabricating C-D or S-D convex spherical gel surfaces for use in cell and tissue culturing and in other surface and interface applications, comprising: a first substrate of a sufficient rigidity having an array or arrays of C-D or S-D convex SSs each of which has same radius or different radii, coated with an appropriate chemical adhesive agent to ensure the strong adherence of the to-be-formed gel layer to these convex SSs;

a second substrate of a sufficient rigidity having an array or arrays of C-D or S-D concave SSs, wherein the pattern of the array or arrays of the C-D or S-D concave SSs is identical to that of the array or arrays of C-D or S-D convex SSs of the first substrate (i.e., the relative orientations and positions of the centerlines of the C-D or S-D concave SSs of this second substrate are identical to those of the centerlines of the C-D or S-D convex SSs of the first substrate), each of these C-D or S-D concave SSs has the radius equal to the radius of the corresponding C-D or S-D convex SS of the first substrate plus the corresponding thickness of the to-be-coated gel layer on this C-D or S-D convex SS of the first substrate, and this second substrate is coated with an appropriate chemical repellent agent to ensure this second substrate can be easily withdrawn or detached from the to-be-exposed convex gel surfaces, coated on the convex SSs of the first substrate, without damaging these to-be-exposed convex gel surfaces;

depending on the thickness of the gel layer to be coated on each of the C-D or S-D convex SSs of the first substrate, an appropriate amount of the gel solution being dropped onto the C-D or S-D convex SSs of the first substrate;

the first and second substrates being oriented and precisely aligned with each other so that the centerline of each of the C-D or S-D concave SSs of the second substrate is precisely aligned with the centerline of the corresponding C-D or S-D convex SS of the first substrate;

the second substrate then being brought to approach to the first substrate to press the gel solution to uniformly re-distribute the gel solution on the C-D or S-D convex SSs of the first substrate, wherein, when the center of a C-D or S-D concave SS of the second substrate is on the center of the corresponding C-D or S-D convex SS of the first substrate (i.e., when a C-D or S-D concave SS of the second substrate and the corresponding C-D or S-D convex SS of the first substrate are concentric), the uniform gap between this C-D or S-D concave SS of the second substrate and the corresponding C-D or S-D convex SS of the first substrate will ensure that, after the polymerization of the gel solution the thickness of the formed gel layer on top of this C-D or S-D convex SS of the first substrate is uniform;

and, after the second substrate is carefully withdrawn from the first substrate, each of the C-D or S-D convex SSs of the first substrate being coated with a gel layer of uniform thickness, wherein the first substrate becomes a substrate with C-D or S-D convex spherical gel surfaces.

Embodiment 45. The method of Embodiment 44, wherein, for the precise alignments between the centerlines and centers of the C-D or S-D concave SSs of the second substrate and the corresponding centerlines and centers of the C-D or S-D convex SS of the first substrate, multiple identification and alignment markers were made on the first and second substrates in the fabrication processes of these substrates to precisely memorize the relative orientations and positions of these substrates when the C-D or S-D convex and concave SSs were generated on these substrates.

Embodiment 46. The method of Embodiment 44, wherein the thickness of the to-be-coated gel layer on each of the C-D or S-D convex SSs of the first substrate can be same or different.

Embodiment 47. The method of Embodiment 44, wherein the first substrate is a micro ball embedded PDMS substrate wherein the array or arrays of C-D or S-D convex SSs of the first substrate are the C-D or S-D convex SSs of an array or arrays of balls which are embedded on the surface of a PDMS layer.

Embodiment 48. The method of Embodiment 44, wherein the first substrate is entirely made of PDMS and the C-D or S-D convex SSs of the first substrate are C-D or S-D convex spherical PDMS surfaces.

Embodiment 49. The method of Embodiment 44, wherein the second substrate is made of PDMS and the C-D or S-D concave SSs of the second substrate are C-D or S-D concave spherical PDMS surfaces.

Embodiment 50. The method of Embodiment 44, wherein the gel comprises PA gel.

Embodiment 51. The method of Embodiment 44, wherein the diameter of each of the C-D or S-D convex SSs of the first substrate is between about one nanometer and about several centimeters or above.

Embodiment 52. The method of Embodiment 44, wherein the thickness of the gel layer to-be-coated on each of the C-D or S-D convex SSs of the first substrate is between about 1 m or below and about 100 m or above.

Embodiment 53. A method of fabricating C-D or S-D concave spherical gel surfaces for use in cell and tissue culturing and in other surface and interface applications, comprising:

a first substrate of a sufficient rigidity having a C-D or S-D convex SS of a desired radius r, coated with an appropriate chemical repellent agent to ensure this first substrate can be easily withdrawn or detached from the to-be-exposed concave gel surface, coated on below the concave SS of the second substrate, without damaging this to-be-exposed concave gel surface;

a second substrate of a sufficient rigidity having a C-D or S-D concave SS of the radius r plus the thickness of the to-be-coated gel layer on this C-D or S-D concave SS of this second substrate, coated with an appropriate chemical adhesive agent to ensure the strong adherence of the to-be-formed gel layer to this concave SS;

depending on the thickness of the gel layer to be coated on the C-D or S-D concave SS of the second substrate, an appropriate amount of the gel solution being dropped onto the C-D or S-D concave SS of the second substrate;

the first and second substrates being oriented and precisely aligned with each other so that the centerline of the C-D or S-D convex SS of the first substrate is precisely aligned with the centerline of the C-D or S-D concave SS of the second substrate;

the first substrate then being brought to approach to the second substrate to press the gel solution to uniformly re-distribute the gel solution on the C-D or S-D concave SS of the second substrate, wherein, when the center of the C-D or S-D convex SS of the first substrate is on the center of the C-D or S-D concave SS of the second substrate (i.e., when the C-D or S-D convex SS of the first substrate and the C-D or S-D concave SS of the second substrate are concentric), the uniform gap between the C-D or S-D convex SS of the first substrate and the C-D or S-D concave SS of the second substrate will ensure that, after the polymerization of the gel solution the thickness of the formed gel layer on top of the C-D or S-D concave SS of the second substrate is uniform;

and, after the first substrate is carefully withdrawn from the second substrate, the C-D or S-D concave SS of the second substrate being coated with the gel layer of a uniform thickness, wherein the second substrate becomes a substrate with a C-D or S-D concave spherical gel surface.

Embodiment 54. The method of Embodiment 53, wherein, for the precise alignments between the centerline and center of the C-D or S-D concave SS of the second substrate and the centerline and center of the C-D or S-D convex SS of the first substrate, multiple identification and alignment markers were made on the first and second substrates in the fabrication processes of these substrates to precisely memorize the relative orientations and positions of these substrates when the C-D or S-D convex and concave SSs were generated on these substrates.

Embodiment 55. The method of Embodiment 53, wherein the first substrate is a micro ball embedded PDMS substrate wherein the C-D or S-D convex SS of the first substrate is the C-D or S-D convex SS of a ball which is embedded on the surface of a PDMS layer.

Embodiment 56. The method of Embodiment 53, wherein the first substrate is entirely made of PDMS and the C-D or S-D convex SS of the first substrate is a C-D or S-D convex spherical PDMS surface.

Embodiment 57. The method of Embodiment 53, wherein the second substrate is made of PDMS and the C-D or S-D concave SS of the second substrate is a C-D or S-D concave spherical PDMS surface.

Embodiment 58. The method of Embodiment 53, wherein the gel comprises PA gel.

Embodiment 59. The method of Embodiment 53, wherein the diameter of the C-D or S-D convex SS of the first substrate is between about one nanometer and about several centimeters or above.

Embodiment 60. The method of Embodiment 53, wherein the thickness of the gel layer to-be-coated on the C-D or S-D concave SS of the second substrate is between about 1 m or below and about 100 m or above.

Embodiment 61. A method of fabricating C-D or S-D concave spherical gel surfaces for use in cell and tissue culturing and in other surface and interface applications, comprising:

a first substrate of a sufficient rigidity having an array or arrays of C-D or S-D convex SSs each of which has same radius or different radii, coated with an appropriate chemical repellent agent to ensure this first substrate can be easily withdrawn or detached from the to-be-exposed concave gel surfaces coated on the concave SSs of the second substrate, introduced as follows, without damaging these to-be-exposed concave gel surfaces;

a second substrate of a sufficient rigidity having an array or arrays of C-D or S-D concave SSs, wherein the pattern of the array or arrays of the C-D or S-D concave SSs is identical to that of the array or arrays of C-D or S-D convex SSs of the first substrate (i.e., the relative orientations and positions of the centerlines of the C-D or S-D concave SSs of this second substrate are identical to those of the centerlines of the C-D or S-D convex SSs of the first substrate), each of these C-D or S-D concave SSs has the radius equal to the radius of the corresponding C-D or S-D convex SS of the first substrate plus the corresponding thickness of the to-be-coated gel layer on this C-D or S-D concave SS of this second substrate, and this second substrate is coated with an appropriate chemical adhesive agent to ensure the strong adherence of the to-be-formed gel layer to these concave SSs;

depending on the thickness of the gel layer to be coated on each of the C-D or S-D concave SSs of the second substrate, an appropriate amount of the gel solution being dropped onto the C-D or S-D concave SSs of the second substrate;

the first and second substrates being oriented and precisely aligned with each other so that the centerline of each of the C-D or S-D convex SSs of the first substrate is precisely aligned with the centerline of the corresponding C-D or S-D concave SS of the second substrate;

the first substrate then being brought to approach to the second substrate to press the gel solution to uniformly re-distribute the gel solution on the C-D or S-D concave SSs of the second substrate, wherein, when the center of a C-D or S-D convex SS of the first substrate is on the center of the corresponding C-D or S-D concave SS of the second substrate (i.e., when a C-D or S-D convex SS of the first substrate and the corresponding C-D or S-D concave SS of the second substrate are concentric), the uniform gap between this C-D or S-D convex SS of the first substrate and the corresponding C-D or S-D concave SS of the second substrate will ensure that, after the polymerization of the gel solution the thickness of the formed gel layer on top of this C-D or S-D concave SS of the second substrate is uniform;

and, after the first substrate is carefully withdrawn from the second substrate, each of the C-D or S-D concave SSs of the second substrate being coated with a gel layer of uniform thickness, wherein the second substrate becomes a substrate with C-D or S-D concave spherical gel surfaces.

Embodiment 62. The method of Embodiment 61, wherein, for the precise alignments between the centerlines and centers of the C-D or S-D concave SSs of the second substrate and the corresponding centerlines and centers of the C-D or S-D convex SS of the first substrate, multiple identification and alignment markers were made on the first and second substrates in the fabrication processes of these substrates to precisely memorize the relative orientations and positions of these substrates when the C-D or S-D convex and concave SSs were generated on these substrates.

Embodiment 63. The method of Embodiment 61, wherein the thickness of the to-be-coated gel layer on each of the C-D or S-D concave SSs of the second substrate can be same or different.

Embodiment 64. The method of Embodiment 61, wherein the first substrate is a micro ball embedded PDMS substrate wherein the array or arrays of C-D or S-D convex SSs of the first substrate are the C-D or S-D convex SSs of an array or arrays of balls which are embedded on the surface of a PDMS layer.

Embodiment 65. The method of Embodiment 61, wherein the first substrate is entirely made of PDMS and the C-D or S-D convex SSs of the first substrate are C-D or S-D convex spherical PDMS surfaces.

Embodiment 66. The method of Embodiment 61, wherein the second substrate is made of PDMS and the C-D or S-D concave SSs of the second substrate are C-D or S-D concave spherical PDMS surfaces.

Embodiment 67. The method of Embodiment 61, wherein the gel comprises PA gel.

Embodiment 68. The method of Embodiment 61, wherein the diameter of each of the C-D or S-D convex SSs of the first substrate is between about one nanometer and about several centimeters or above.

Embodiment 69. The method of Embodiment 61, wherein the thickness of the gel layer to-be-coated on each of the C-D or S-D concave SSs of the second substrate is between about 1 m or below and about 100 m or above.

The Third Aspect of the Disclosure

Substrates with Simple Varying Surface Curvatures—

C-D convex and concave SSs have uniform surface shapes, i.e., the through-center normal cross-sections of these SSs are circular and have single invariant curvatures, equal to the inverses of the radii of these SSs, along their circumferences. According to our cell experimental findings summarized in the above Section of "Cell Experimental Findings—" in "Background", the following three types of C-D convex (see FIG. 3$a1$, b1, c1) and concave (see FIG. 3$a2$, b2, c2) substrates may be designed and fabricated to present simple varying surface shapes to direct cell attachment, spreading, and migration. The normal cross-section of the surface of each of these three types of substrates has a varying curvature or has two or more curvatures.

Figure 3:
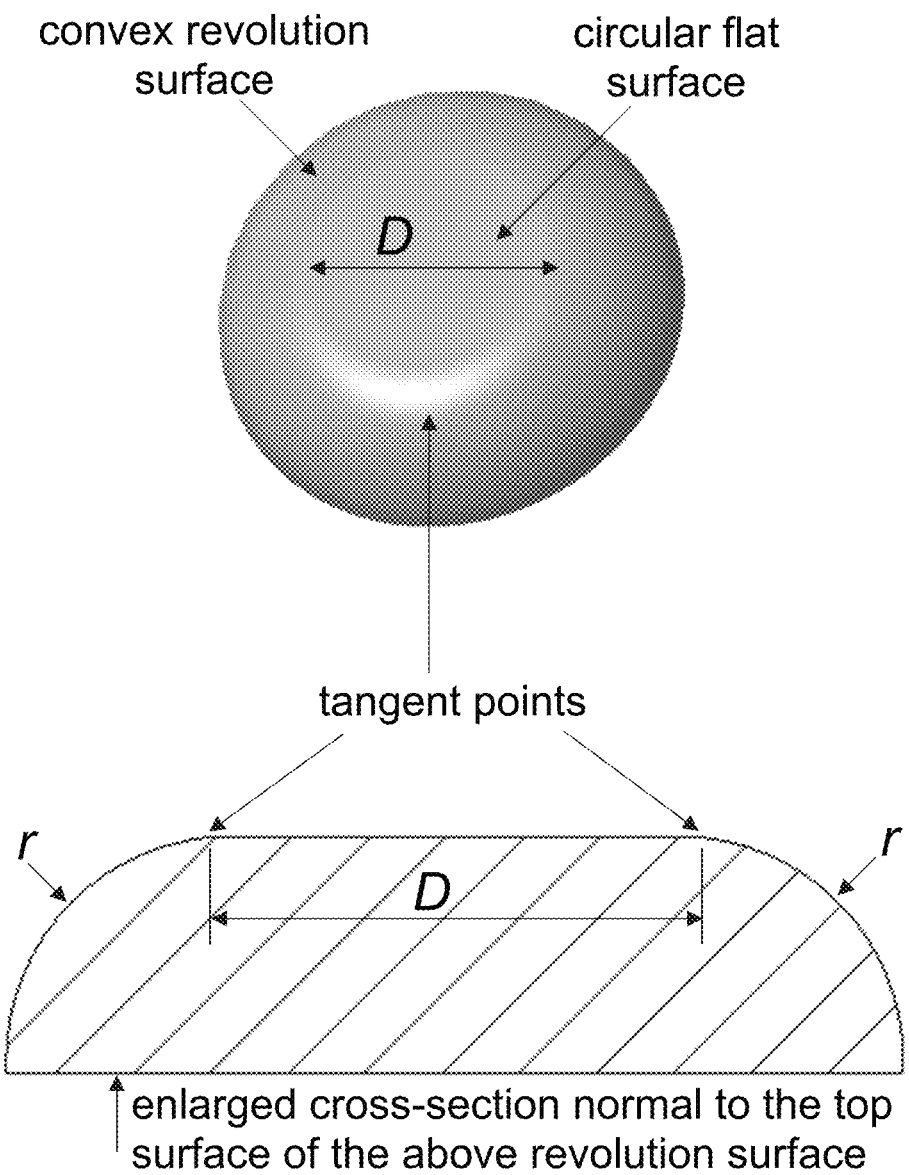
FIG. 3 illustrates the three types of C-D or S-D convex (a1, b1, c1) and concave (a2, b2, c2) substrates with varying surface shapes (i.e., with varying surface curvatures) that are used to direct cell attachment, spreading, and migration according to the present invention.
Figure 3:
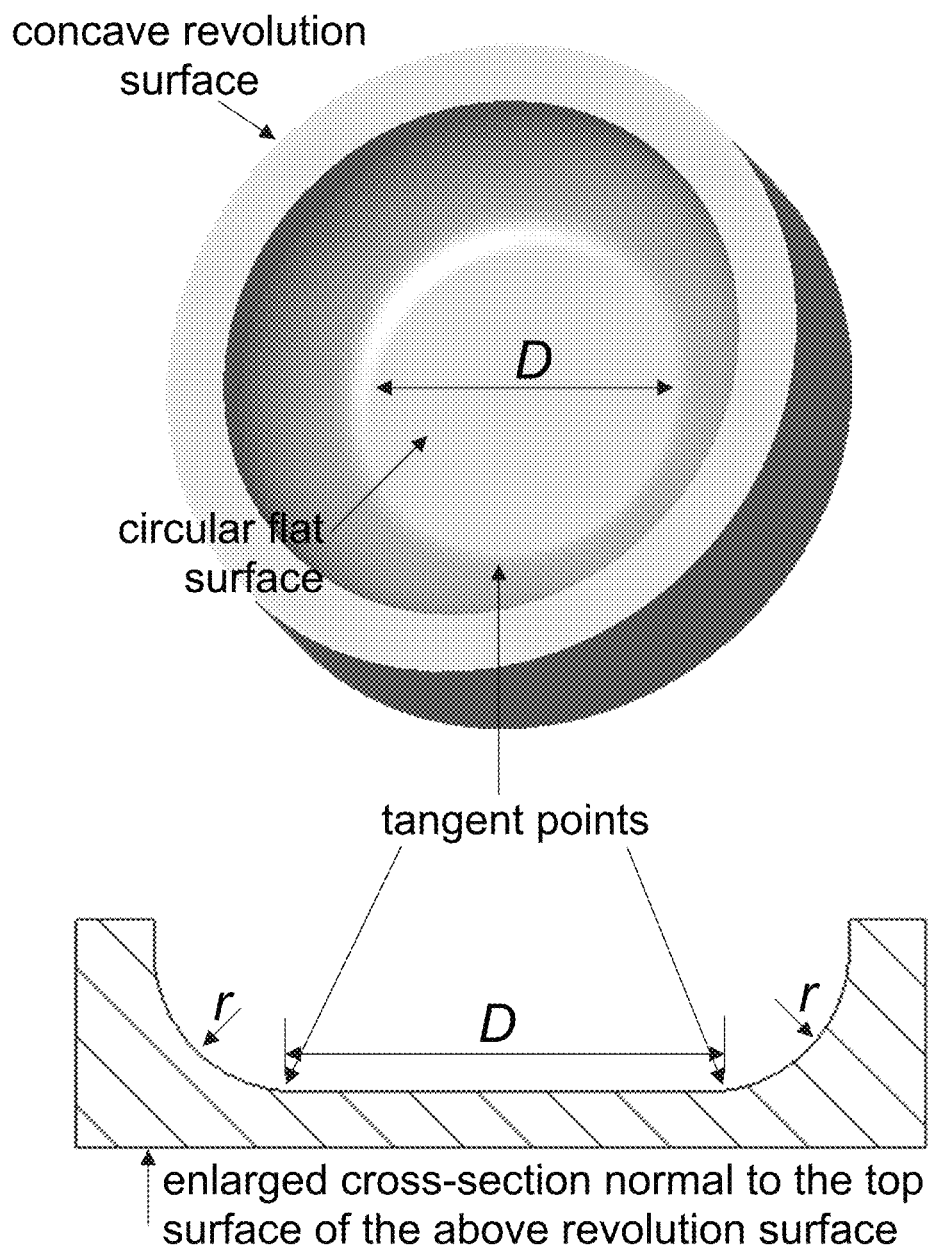
Figure 3:
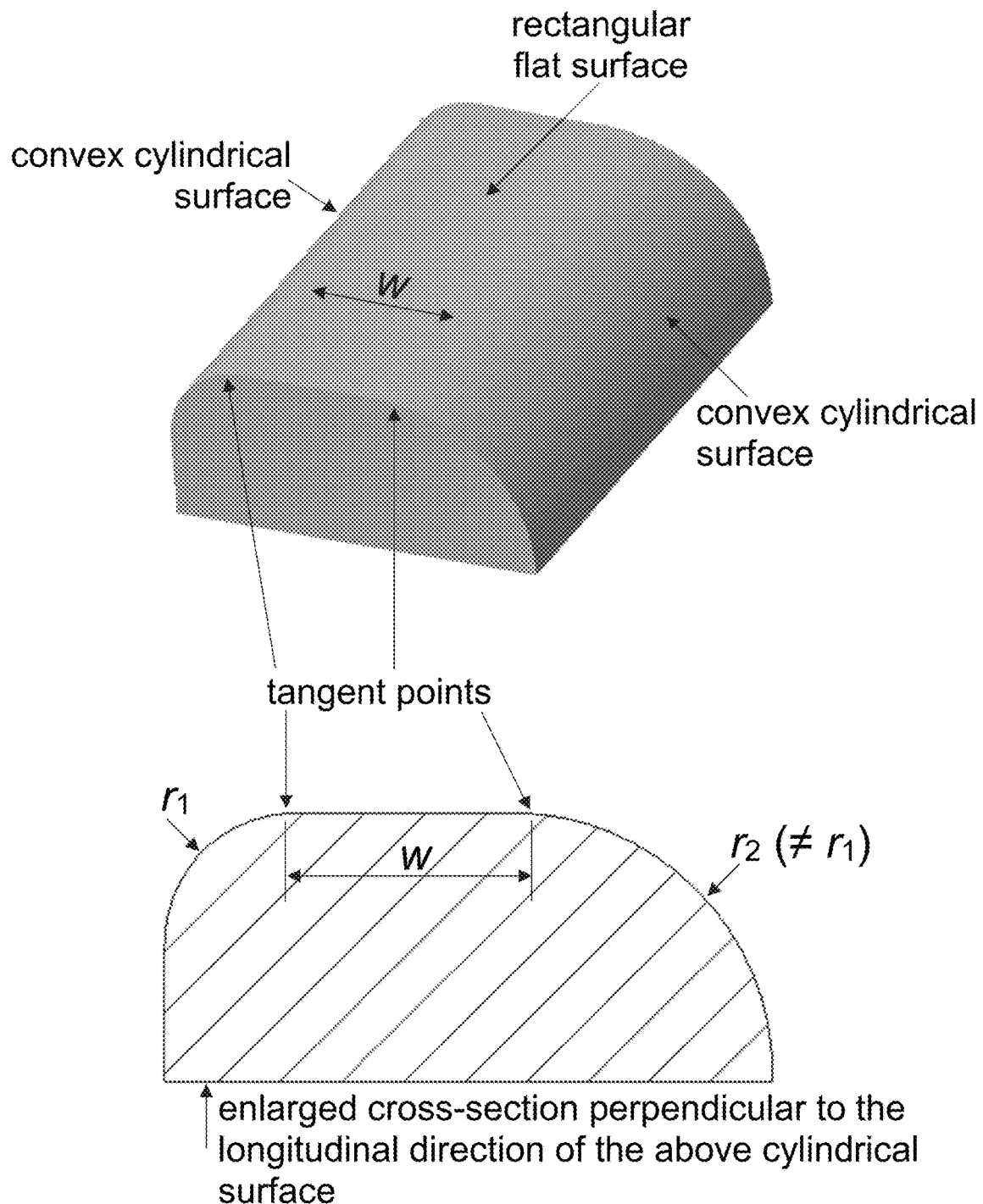
Figure 3:
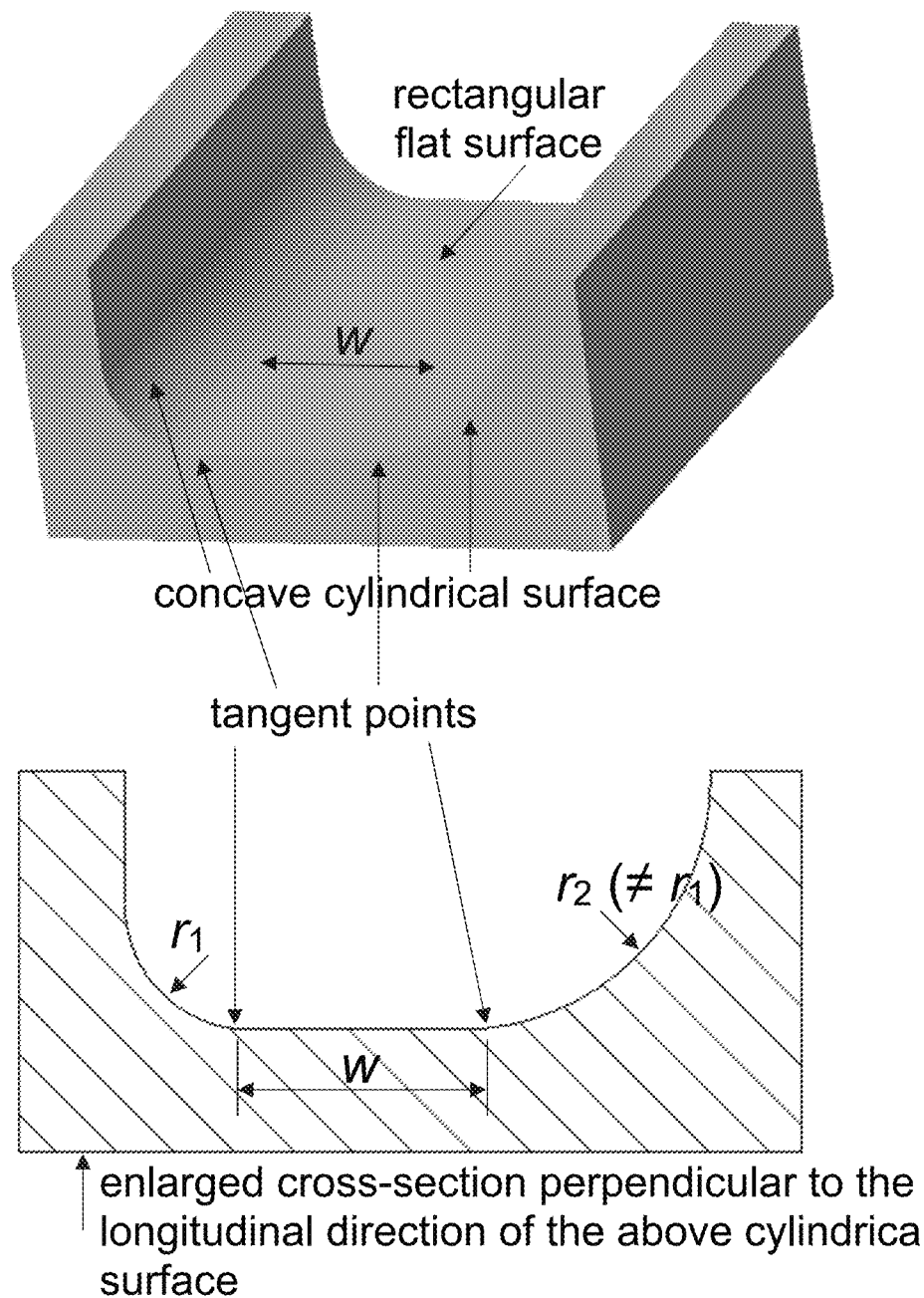
Figure 3:
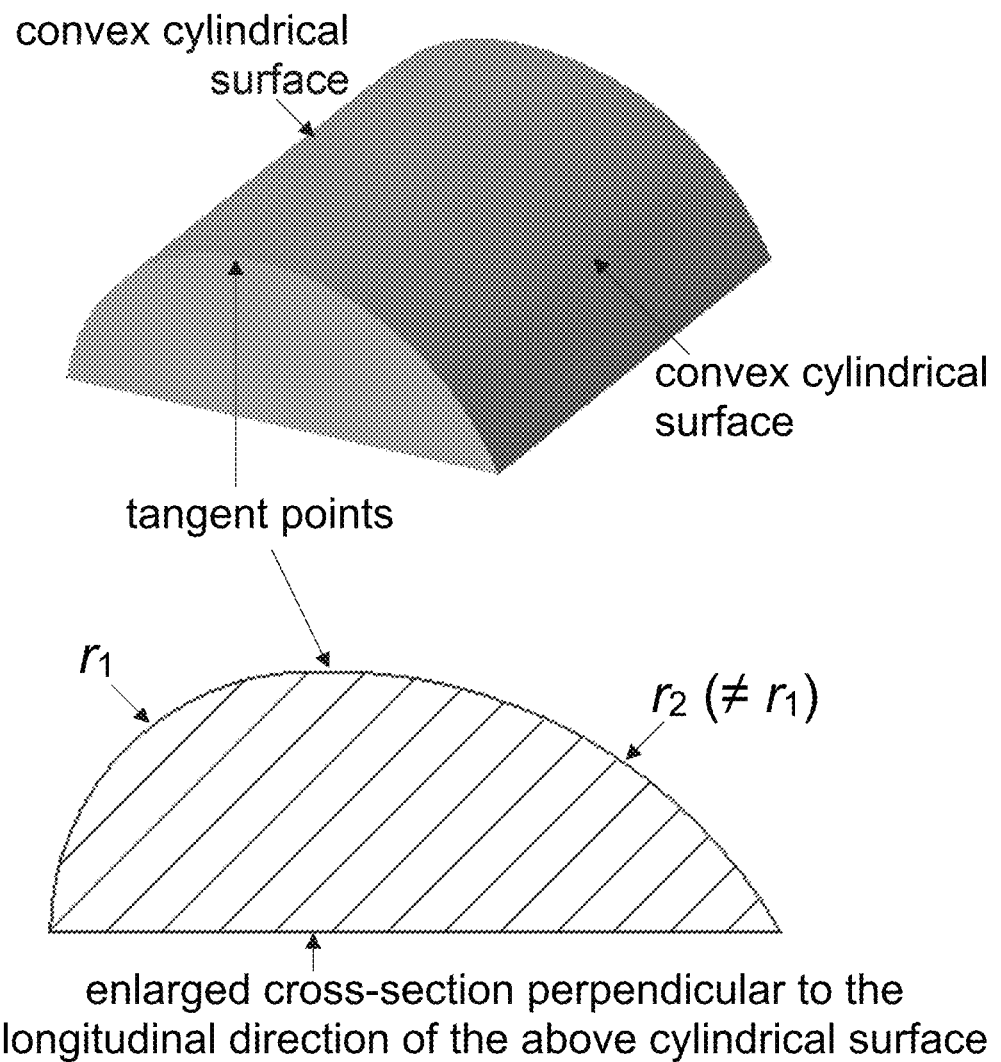
Figure 3:
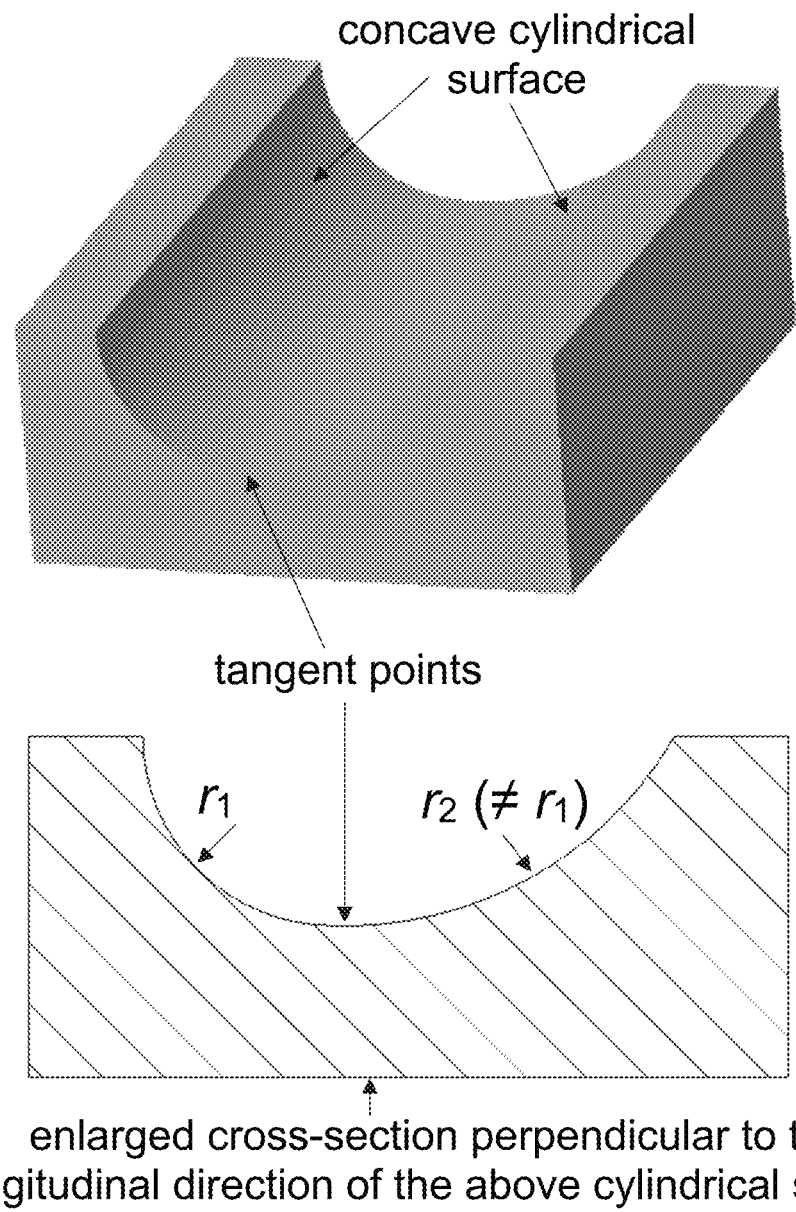

(1) Substrates have revolution surfaces whose through-center normal cross-sections consist of a segment of horizontal straight line (D) and two symmetric circular arcs with the desired radius (r) tangent to the two ends of this segment of straight line (see FIG. 3$a1$ and a2). The through-center normal cross-section of the surface of each of these substrates has two curvatures with one being the zero curvature of the segment of horizontal straight line and the other being the nonzero curvature of each of the two symmetric circular arcs in this normal cross-section. This type of shape-varying substrates provides smooth surfaces having the shape-variation settings of from a circular flat surface to a curved surface with a defined uniform shape and vice versa. If a cell is cultured on such a substrate, in the presence of cell culture media, the attachment, spreading, and migration of this cell are confined in the circular flat part by the curved part of the smooth revolution surface of this substrate.

(2) Substrates have cylindrical surfaces whose normal cross-sections (which are perpendicular to the longitudinal directions of these cylindrical surfaces) consist of a segment of horizontal straight line (w) and two circular arcs with the desired different radii ($r_1$ and $r_2$) tangent to the two ends of this segment of straight line (see FIG. 3$b1$ and b2). The normal cross-section of the surface of each of these substrates has three curvatures with one being the zero curvature of the segment of horizontal straight line sandwiched between the other two being the nonzero curvatures of the two circular arcs attached at the two ends of this segment of straight line in this normal cross-section. This type of shape-varying substrates provides smooth surfaces having the shape-variation settings of from a rectangular flat surface to two curved surfaces with defined different uniform shapes that are respectively located at the two longitudinal sides of this rectangular flat surface and vice versa. If a cell is cultured on such a substrate, in the presence of cell culture media, the attachment, spreading, and migration of this cell are confined in the rectangular flat part by the two curved parts (that are respectively located at the two longitudinal sides of the rectangular flat part) of the smooth cylindrical surface of this substrate.

(3) Substrates have cylindrical surfaces whose normal cross-sections (which are again perpendicular to the longitudinal directions of these cylindrical surfaces) consist of two smoothly-connected (i.e., tangent) circular arcs with the desired different radii ($r_1$ and $r_2$) (see FIG. 3$c1$ and c2). The normal cross-section of the surface of each of these substrates has two different nonzero curvatures which are the curvatures of the two circular arcs in this normal cross-section. This type of shape-varying substrates provides smooth surfaces having the shape-variation settings of from a curved surface with a defined curvature to another curved surface with a defined different curvature. If a cell is cultured on such a substrate, in the presence of cell culture media, the confinement of the curved surface with the larger curvature of the smooth cylindrical surface of this substrate to the attachment, spreading, and migration of this cell is larger compared with that of the other curved surface with the smaller curvature of the smooth cylindrical surface of this substrate.

The time-lapse curvature-dependent spreading and migration responses of the stem cells cultured on these three types of shape-varying substrates may be investigated. The results of these experiments will reveal the stem cells' abilities to recognize and to respond to surface curvatures and the stem cells' abilities to differentiate and to respond to curvature variations or curvature differences. Since surface curvatures create height differences between different locations on curved surfaces, together with the results of the experiments in the above Section of "Substrate Curvature Effects of Focal Adhesion Strength and Contractile Actomyosin Apparatus—" for the stem cells cultured on convex and concave SSs, the results of the experiments here in this Section will also reveal the stem cells' abilities to differentiate and to respond to the height differences on the surface of a substrate.

The third aspect of the disclosure provides the following non-limiting embodiments (the numbering of these embodiments is continued from that of the embodiments provided by the first and second aspects of the disclosure listed in the above):

Embodiment 70. A method of using C-D or S-D convex and concave surfaces with varying curvatures to direct cell attachment, spreading, and migration, comprising:

culturing a cell on a substrate with a smooth revolution surface, having the shape-variation setting of from a circular flat surface to a curved surface, in the presence of cell culture media, wherein the attachment, spreading, and migration of this cell are confined in the circular flat part by the curved part of this smooth revolution surface.

Embodiment 71. The method of Embodiment 70, wherein the substrate is selected from the group consisting of a convex substrate, a concave substrate, and combinations thereof.

Embodiment 72. The method of Embodiment 70, wherein the normal cross-section of the curved part of the smooth revolution surface of the substrate comprises two symmetric circular arcs having a uniform curvature or radius.

Embodiment 73. The method of Embodiment 70, wherein the two symmetric circular arcs of the normal cross-section of the curved part of the smooth revolution surface of the substrate comprise a radius of between about several micrometers or below and about several centimeters or above.

Embodiment 74. The method of Embodiment 70, wherein the circular flat part of the smooth revolution surface of the substrate comprises a radius of between about several micrometers or below and about several centimeters or above.

Embodiment 75. The method of Embodiment 70, wherein the substrate comprises a coating selected from the group consisting of a cell adhesive, a cell adhesion-promotor, a cell repellent, or a combination thereof.

Embodiment 76. The method of Embodiment 70, wherein a material of the substrate comprises a PDMS, glass, gel, plastic, silica, silicone, ceramic, metal, silicon, or silicon nitride.

Embodiment 77. The method of Embodiment 70, wherein the substrate comprises an array of substrates each of which has a smooth revolution surface having the shape-variation setting of from a circular flat surface to a curved surface.

Embodiment 78. A method of using C-D or S-D convex and concave surfaces with varying curvatures to direct cell attachment, spreading, and migration, comprising:

culturing a cell on a substrate with a smooth cylindrical surface, having the shape-variation setting of from a rectangular flat surface to two curved surfaces that are respectively located at the two longitudinal sides of the rectangular flat surface, in the presence of cell culture media, wherein the attachment, spreading, and migration of this cell are confined in the rectangular flat part by the two curved parts (that are respectively located at the two longitudinal sides of the rectangular flat part) of this smooth cylindrical surface.

Embodiment 79. The method of Embodiment 78, wherein the substrate is selected from the group consisting of a convex substrate, a concave substrate, and combinations thereof.

Embodiment 80. The method of Embodiment 78, wherein the normal cross-section of each of the two curved parts of the smooth cylindrical surface of the substrate comprises a circular arc, and the two circular arcs of the normal cross-sections of these two curved parts have different or same radii.

Embodiment 81. The method of Embodiment 80, wherein the confinements of the two curved parts of the smooth cylindrical surface of the substrate to the attachment, spreading, and migration of a cell on this substrate are different if the two circular arcs of the normal cross-sections of these two curved parts have different radii, and this confinement is larger if the corresponding circular arc of the normal cross-section of one of these two curved parts has a larger radius.

Embodiment 82. The method of Embodiment 80, wherein the circular arc of the normal cross-section of each of the two curved parts of the smooth cylindrical surface of the substrate comprises a radius of between about several micrometers or below and about several centimeters or above.

Embodiment 83. The method of Embodiment 78, wherein the rectangular flat part of the smooth cylindrical surface of the substrate comprises a length and a width of between about several micrometers or below and about several centimeters or above.

Embodiment 84. The method of Embodiment 78, wherein the substrate comprises a coating selected from the group consisting of a cell adhesive, a cell adhesion-promotor, a cell repellent, or a combination thereof.

Embodiment 85. The method of Embodiment 78, wherein a material of the substrate comprises a PDMS, glass, gel, plastic, silica, silicone, ceramic, metal, silicon, or silicon nitride.

Embodiment 86. The method of Embodiment 78, wherein the substrate comprises an array of substrates each of which has a smooth cylindrical surface having the shape-variation setting of from a rectangular flat surface to two curved surfaces that are respectively located at the two longitudinal sides of the rectangular flat surface.

Embodiment 87. A method of using C-D or S-D convex and concave surfaces with varying curvatures to direct cell attachment, spreading, and migration, comprising:

culturing a cell on a substrate with a smooth cylindrical surface, having the shape-variation setting of from a curved surface with a defined curvature to another curved surface with a defined different curvature, in the presence of cell culture media, wherein the confinement of the curved surface with the larger curvature of the smooth cylindrical surface of the substrate to the attachment, spreading, and migration of this cell is larger compared with that of the other curved surface with the smaller curvature of the smooth cylindrical surface of the substrate.

Embodiment 88. The method of Embodiment 87, wherein the substrate is selected from the group consisting of a convex substrate, a concave substrate, and combinations thereof.

Embodiment 89. The method of Embodiment 87, wherein the normal cross-section of each of the two curved surfaces of the smooth cylindrical surface of the substrate comprises a circular arc, and the two circular arcs of the normal cross-sections of the smooth cylindrical surface of the substrate have different or same radii.

Embodiment 90. The method of Embodiment 87, wherein the circular arc of the normal cross-section of each of the two curved surfaces of the smooth cylindrical surface of the substrate comprises a radius of between about several micrometers or below and about several centimeters or above.

Embodiment 91. The method of Embodiment 87, wherein the substrate comprises a coating selected from the group consisting of a cell adhesive, a cell adhesion-promotor, a cell repellent, or a combination thereof.

Embodiment 92. The method of Embodiment 87, wherein a material of the substrate comprises a PDMS, glass, gel, plastic, silica, silicone, ceramic, metal, silicon, or silicon nitride.

Embodiment 93. The method of Embodiment 87, wherein the substrate comprises an array of substrates each of which has a smooth cylindrical surface having the shape-variation setting of from a curved surface with a defined curvature to another curved surface with a defined different curvature.

All publications and patent documents cited in this application are incorporated by reference in pertinent part for all purposes to the same extent as if each individual publication or patent document were so individually denoted. By citation of various references in this document, the applicant does not admit any particular reference is "prior art" to their invention.

Discussion

Substrate Curvature-Dependent Stem Cell Mechanics—

Based on the results of the above-proposed experiments of stem cells cultured on the C-D concave and convex surfaces with normal cross-sections having single invariant curvatures invented in the present disclosure and of stem cells cultured on the C-D convex and concave surfaces with normal cross-sections having varying curvatures invented in the present disclosure, the relevant substrate curvature-dependent mechanics and energetics of stem cells at both the continuum and molecular levels may be developed (Sanz-Herrera et al., 2009; Jacobs et al., 2012; Rodriguez et al., 2013; Cheng et al., 2017; Cheng et al., 2017-2; Nicolas, 2017; Spill and Zaman, 2017; Vassaux and Milan, 2017; Wu et al., 2017; Kaunas and Zemel, 2018), and the following two questions may be specifically answered, how a stem cell senses the curvature and curvature variation of a surface, and how this stem cell makes the decision on which direction to spread and migrate on a curved and curvature-varying surface. The answers to these two questions will be compared with those to the following two similar questions for stem cells cultured on substrates with varying rigidities, how a stem cell senses the rigidity variation of a substrate, and how this stem cell makes the decision on which direction to spread and migrate on a rigidity-varying substrate (Lo et al., 2000; Tang et al., 2012). All these are necessary for understanding the behaviors of stem cells in 3D micromechanical environments and for designing scaffolds to effectively and efficiently control the development of stem cells and the resulting tissues for tissue engineering and regenerative medicine (Zadpoor, 2015; Zhang et al., 2017; Winkler et al., 2018; Li et al., 2019; Przekora, 2019; Velmurugan et al., 2019; Zhang et al., 2019).

Quantitative Equivalency Between SSs and PA Gels and PDMS Micropost Arrays in Influencing/Inducing Stem Cell Differentiation—

For the possible biophysical mechanisms and biomolecular signaling pathways of the observed differentiation responses of the stem cells to the mechanical factors, cell contractility plays a critical role in all the observed differentiation responses of the stem cells growing on the PA gels (Engler et al., 2006; Swift et al., 2013; Ivanovska et al., 2015), PDMS micropost arrays (Fu et al., 2010), and planar geometrically defined micro-patterns (Kilian et al., 2010; Wan et al., 2010; Song et al., 2011; Yao et al., 2013; Bao al., 2018; von Erlach et al., 2018). Compared with the case of the PA gels where the different moduli of elasticity of the substrate PA gels are the inducements and the case of the PDMS micropost arrays where the different rigidities of the substrate PDMS micropost arrays are the inducements of the observed different differentiation responses of the hMSCs, here as summarized in the above Section of "Cell Experimental Findings—" in "Background", substrate curvatures alone can induce differentiation of hMSCs since the MGBs all have infinitely-high moduli of elasticity and infinitely-high surface rigidities with respect to those of the cells. But, since substrate curvature also modulates cell contractility, the observed differentiation response of the hMSCs growing on the MGBs is likely sharing the same or similar fundamental biophysical mechanisms and biomolecular signaling pathways with the observed differentiation responses of the hMSCs growing on the PA gels and PDMS micropost arrays. These same or similar fundamental biophysical mechanisms and biomolecular signaling pathways have to be related to the following observed characteristics of the low cell contractility of the cells growing on the soft substrates (with moduli of elasticity similar to those of fat) with respect to the high cell contractility of the same type of cells growing on the stiff substrates (with moduli of elasticity similar to or much larger than those of bone): low cell tension, low cell spread area, poorly developed focal adhesions and stress fibers, lower levels of lamin-A,C in the nuclear lamina, and transcription factors RAR-γ and YAP/TAZ remain in the cytoplasm, which favor adipogenesis (Ivanovska et al., 2015).

However, the spreading morphologies of the hMSCs on the MGBs, which are majorly the spindle shapes (Lee and Yang, 2017), are very different from those of the hMSCs on the PA gels and PDMS micropost arrays, which can be from the round shapes to the well-spread shapes depending on the substrate rigidity (Engler et al., 2006; Fu et al., 2010; Swift et al., 2013; Ivanovska et al., 2015). The sizes, strengths, numbers, and distributions of the focal adhesions and stress fibers of the hMSCs on the MGBs can then be very different from those of the focal adhesions and stress fibers of the hMSCs on the PA gels and PDMS micropost arrays. The detailed mechanosensing mechanism of the bent or misaligned configuration of the contractile actomyosin apparatus (Sanz-Herrera et al., 2009) of the hMSCs on the MGBs can also be different from the detailed mechanosensing mechanisms of the contractile actomyosin apparatus of the hMSCs on the (flat) PA gels and (flat) PDMS micropost arrays. More fundamentally, cells mechanosense the elasticity of the substrate PA gels and the rigidity of the substrate PDMS micropost arrays only through focal adhesions, and the elasticity of the substrate PA gels and the rigidity of the substrate PDMS micropost arrays modulate the developments of focal adhesions, stress fibers, and contractile actomyosin apparatus at the same time in a coupled fashion, whereas here cells mechanosense the surface curvatures of the MGBs through focal adhesions, stress fibers, and contractile actomyosin apparatus at the same time, i.e., surface curvatures directly and independently modulate the developments of focal adhesions, stress fibers, and contractile actomyosin apparatus at the same time, and the developments of these three cellular components on the curved surfaces also modulate with respect to each other at the same time in a coupled fashion as in the cases of cells on the PA gels and PDMS micropost arrays.

Note that, in making the MGB embedded PA gels, MGB embedded PDMS substrates, PDMS substrates with convex spherical PDMS surfaces, PDMS substrates with concave SSs, and PDMS substrates with convex and concave spherical PA gel surfaces, the height of the final convex SSs or the depth of the final concave SSs of a substrate measured from the surrounding flat PA gel or PDMS surface may be controlled. In some experiments, these heights and depths may be decreased to small enough so that a stem cell will spread on both a convex or concave SS and its surrounding flat PA gel or PDMS surface, and then the modulation effects of locally-curved substrates or local substrate curvatures on the spreading and on the distributions of the focal adhesions and stress fibers of a stem cell may be studied. This may further elucidate the effects of substrate curvatures on the developments of focal adhesions and stress fibers.

Nevertheless, due to the possibly-same or similar fundamental biophysical mechanisms and biomolecular signaling pathways for the observed differentiation responses of the hMSCs growing on the MGBs and on the PA gels and PDMS micropost arrays, the quantitative equivalency between the decreased cell contractility of the hMSCs on the smaller MGBs or on the C-D convex and concave SSs of the other types (i.e., the spherical PDMS surfaces described in the above Section of "Concave and Convex Spherical PDMS Surfaces—" in "The First Aspect of the Disclosure" of the "Detailed Description of the Disclosure", and the spherical PA gel surfaces described in the above Section of "C-D Convex and Concave Spherical PA Gel Surfaces—" in "The Second Aspect of the Disclosure" of the "Detailed Description of the Disclosure") with smaller radii and the decreased cell contractility of the hMSCs on the softer PA gels and softer PDMS micropost arrays, in terms of the observed matrix elasticity-dependent levels of lamin-A,C in the nuclear lamina and transcription factors RAR-γ and YAP/TAZ in the nucleus (Swift et al., 2013; Ivanovska et al., 2015), may also be sought. This quantitative equivalency, between the increase of substrate curvature and the decrease of substrate matrix elasticity and substrate rigidity, in influencing/inducing stem cell differentiation will be correlated to the same quantitative equivalency in terms of the induced reductions of mean cell spread area and mean in-plane cellular traction force discussed in the above Section of "Substrate Curvature Effects of Focal Adhesion Strength and Contractile Actomyosin Apparatus—" in "The Second Aspect of the Disclosure" of the "Detailed Description of the Disclosure". The threshold diameters or radii of the MGBs or C-D convex and concave SSs of the other types at which hMSCs significantly start to differentiate may be found out, and the relevant quantitative results will largely contribute to the establishments of the possible biophysical mechanisms and biomolecular signaling pathways for the observed differentiation responses of hMSCs to substrate curvatures.

Combined Effects of Substrate Curvature and Matrix Elasticity on Stem Cell Differentiation—

It will also be necessary to investigate the differentiation responses of the hMSCs cultured on the convex and concave spherical PA gel surfaces which will be compared with those of the hMSCs cultured on the MGBs and flat PA gel surfaces, and these comparisons will reveal the combined effects of surface curvature and matrix elasticity on the differentiations of the stem cells.

This study will enhance our existing understanding on the specific role of substrate matrix elasticity in inducing the observed stem cell differentiation (Ivanovska et al., 2015; Cheng et al., 2017). This study will be useful in identifying the specific roles of cell tension, cell shape, cell spread area, and cell stiffness, the extents of their influences and their combinational effects, and the biomolecular signaling pathways of the mechanosensing and mechanotransduction processes for cell tension, cell shape, cell spread area, and cell stiffness to play their roles, in inducing the observed differentiation responses of the stem cells to the mechanical factors including substrate geometries, substrate matrix elasticity, and substrate rigidity. This study will also be useful in identifying the direct-involvements and specific roles of focal adhesions, stress fibers, and contractile actomyosin apparatus in the biomolecular signaling pathways of the mechanosensing and mechanotransduction processes for the translocations of the relevant transcription factors to the nucleus and for the relevant gene expressions in the nucleus in the observed stem cell differentiations induced by matrix elasticity, which are separate from the established indirect-involvements of these three cellular components in these mechanosensing and mechanotransduction processes through the resulted matrix elasticity-dependent cell contractility (or cell tension, which is believed to be the biophysical quantity that decides the matrix elasticity-dependent stem cell differentiation) (Dingal and Discher, 2014; Ivanovska et al., 2015; Cheng et al., 2017).

Deforming the Nucleus of a Stem Cell—

It is clear that the deformation of the nucleus induced by the topography of the environment of a stem cell or by the mechanical stresses exerted on a stem cell regulates the gene expressions of the stem cell (Liu et al., 2016; Anselme et al., 2018). As summarized in the above Section of "Cell Experimental Findings—" in "Background", the curvature of the substrate restricts the spreading of a stem cell and this restriction is larger when the curvature of the substrate is larger. Then the curvature of the substrate also naturally indirectly deforms the nucleus inside the stem cell accordingly, and therefore the C-D culturing technology here may also be used as an effective tool to deform the nucleus of a stem cell. The convex and concave C-D surfaces invented in the present disclosure may be used to and other C-D surfaces may be designed and fabricated to induce some unique and interesting deformations of the nucleus inside a stem cell, and the correlation between the induced-deformation or its resulting shape, size, and tension of the nucleus of a stem cell due to surface curvature and the inducing surface curvature may be sought. The roles of the induced-deformation or its resulting shape, size, and tension of the nucleus of a stem cell due to surface curvature, and the possible corresponding biophysical mechanisms and biomolecular signaling pathways for the involvements of these nuclear parameters in the mechanosensing and mechanotransduction processes for the relevant gene expressions in the nucleus, in inducing the observed differentiation responses of this stem cell, may be studied. This study will add to our existing understandings on the mechanosensing and mechanotransduction processes of the nucleus of a stem cell in gene expression, which clearly constitute the final and decisive step of the entire mechanosensing and mechanotransduction process (which also includes the mechanosensing and mechanotransduction processes of the peripheral cellular components including cell focal adhesions, stress fibers, and contractile actomyosin apparatus) of a stem cell for the observed differentiation responses to the mechanical factors.

All patents, patent applications, and publications referred to or cited herein are incorporated by reference in their entirety, including all figures and tables, to the extent they are not inconsistent with the explicit teachings of this specification. By citation of various references in this document, the Applicant does not admit any particular reference is "prior art" to the present invention.

It should be understood that the embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the disclosure without limitation thereto.

REFERENCES

Ankam S, Suryana M, Chan L Y, Moe A A K, Teo B K K, et al. (2013) Substrate topography and size determine the fate of human embryonic stem cells to neuronal or glial lineage. *Acta Biomaterialia* 9: 4535-4545.

Anselme K, Wakhloo N T, Rougerie P, Pieuchot L (2018) Role of the nucleus as a sensor of cell environment topography. Adv Healthcare Mater 7: 1701154.

Aragona M, Panciera T, Manfrin A, Giulitti S, Michielin F, et al. (2013) A mechanical checkpoint controls multicellular growth through YAP/TAZ regulation by actin-processing factors. *Cell* 154: 1047-1059.

Bao M, Xie J, Huck W T S (2018) Recent advances in engineering the stem cell microniche in 3D. *Adv Sci* 5: 1800448.

Baptista D, Teixeira L, van Blitterswijk C, Giselbrecht S, Truckenmuller R (2019) Overlooked? underestimated? Effects of substrate curvature on cell behavior. *Trends Biotechnol* 37: 838-854.

Buxboim A, Rajagopal K, Brown A E X, Discher D E (2010) How deeply cells feel: methods for thin gels. *J Phys Condens Matter* 22: 194116.

Byun I, Kim B (2014) Fabrication of three-dimensional PDMS microstructures by selective bonding and cohesive mechanical failure. *Microelectron Eng* 121: 92-95.

Charrier E E, Pogoda K, Wells R G, Janmey P A (2018) Control of cell morphology and differentiation by substrates with independently tunable elasticity and viscous dissipation. *Nat Commun* 9: 449.

Cheng B, Lin M, Huang G, Li Y, Ji B, et al. (2017) Cellular mechanosensing of the biophysical microenvironment: a review of mathematical models of biophysical regulation of cell responses. *Phys Life Rev* 22-23: 88-119.

Cheng B, Lin M, Huang G, Li Y, Ji B, et al. (2017) Energetics: an emerging frontier in cellular mechanosensing—Reply to comments on "Cellular mechanosensing of the biophysical microenvironment: A review of mathematical models of biophysical regulation of cell responses". *Phys Life Rev* 22-23: 130-135.

Colin-York H, Eggeling C, Fritzsche M (2017) Dissection of mechanical force in living cells by super-resolved traction force microscopy. *Nat Protoc* 12: 783-796.

Dalby M J, Gadegaard N, Tare R, Andar A, Riehle M O, et al. (2007) The control of human mesenchymal cell differentiation using nanoscale symmetry and disorder. *Nat Mater* 6: 997-1003.

Dembo M, Wang Y-L (1999) Stresses at the cell-to-substrate interface during locomotion of fibroblasts. *Biophys J* 76: 2307-2316.

Dingal PCDP, Discher D E (2014) Systems mechanobiology: tension-inhibited protein turnover is sufficient to physically control gene circuits. *Biophys J* 107: 2734-2743.

Engler A J, Sen S, Sweeney H L, Discher D E (2006) Matrix elasticity directs stem cell lineage specification. *Cell* 126: 677-689.

Fernandes T G, Diogo M M, Cabral J M S, "*Stem Cell Bioprocessing: For Cellular Therapy, Diagnostics and Drug Development*", Chapter 5: Microscale technologies for stem cell culture. Woodhead Publishing Limited, Cambridge, UK, 2013, 143-175.

Franck C, Maskarinec S A, Tirrell D A, Ravichandran G (2011) Three-dimensional traction force microscopy: a new tool for quantifying cell-matrix interactions. *PLoS ONE* 6: e17833.

Fu J, Wang Y-K, Yang M T, Desai R A, Yu X, et al. (2010) Mechanical regulation of cell function with geometrically modulated elastomeric substrates. *Nat Methods* 7: 733-736.

Irimia D, Chapter 10: Cell migration in confined environments. In "*Methods in Cell Biology, Volume 121—Micropatterning in Cell Biology, Part C*", Edited by Piel M, Thery M, Elsevier, Amsterdam, Netherlands, 2014, 141-153.

Ivanovska I L, Shin J-W, Swift J, Discher D E (2015) Stem cell mechanobiology: diverse lessons from bone marrow. *Trends Cell Biol* 25: 523-532.

Jacobs C R, Huang H, Kwon R Y, "*Introduction to Cell Mechanics and Mechanobiology*", Garland Science, New York, USA, 2012.

Kaunas R, Zemel A, "*Cell and Matric Mechanics*", CRC Press, Boca Raton, Fla., USA, 2018.

Kilian K A, Bugarija B, Lahn B T, Mrksich M (2010) Geometric cues for directing the differentiation of mesenchymal stem cells. *Proc Natl Acad Sci USA* 107: 4872-4877.

Kim A A, Nekimken A L, Fechner S, O'Brien L E, Pruitt B L, Chapter 12: Microfluidics for mechanobiology of model organisms. In "*Methods in Cell Biology, Volume 146—Microfluidics in Cell Biology Part A: Microfluidics for Multicellular Systems*", Edited by Doh J, Fletcher D, Piel M, Elsevier, Amsterdam, Netherlands, 2018, 217-259.

Kurabayashi K, Huang N-T, Tung Y-C, Chapter 16: Multiscale, hierarchical integration of soft polymer micro- and nanostructures into optical MEMS. In "*Optical Nano and Micro Actuator Technology*", Edited by Knopf G K, Otani Y, Taylor & Francis Group, Abingdon, UK, 2013, 491-518.

Lee F, Iliescu C, Yu F, Yu H, Chapter 3: Constrained spheroids/organoids in perfusion culture. In "*Methods in Cell Biology, Volume 146—Microfluidics in Cell Biology Part A: Microfluidics for Multicellular Systems*", Edited by Doh J, Fletcher D, Piel M, Elsevier, Amsterdam, Netherlands, 2018, 43-65.

Lee S J, Yang S (2012) Micro glass ball embedded gels to study cell mechanobiological responses to substrate curvatures. *Rev Sci Instr* 83: 094302.

Lee S J, Yang S (2017) Substrate curvature restricts spreading and induces differentiation of human mesenchymal stem cells. *Biotechnol J* 12: 1700360.

Li L, Lu H, Zhao Y, Luo J, Yang L, et al. (2019) Functionalized cell-free scaffolds for bone defect repair inspired by self-healing of bone fractures: a review and new perspectives. *Mat Sci Eng C* 98: 1241-1251.

Li M, Dang D, Liu L, Xi N, Wang Y (2017) Atomic force microscopy in characterizing cell mechanics for biomedical applications: a review. *IEEE T Nanobiosci* 16: 523-540.

Liu C, "Foundations of MEMS", 2nd Edition, Pearson, Hoboken, N.J., USA, 2012.

Liu X, Liu R, Cao B, Ye K, Li S, et al. (2016) Subcellular cell geometry on micropillars regulates stem cell differentiation. *Biomaterials* 111: 27-39.

Lo C-M, Wang H-B, Dembo M, Wang Y-L (2000) Cell movement is guided by the rigidity of the substrate. *Biophys J* 79: 144-152.

Madou M J, "*Fundamentals of Microfabrication and Nanotechnology, Three-Volume Set*", CRC Press, Boca Raton, Fla., USA, 2011.

Maloney J M, Walton E B, Bruce C M, Van Vliet K J (2008) Influence of finite thickness and stiffness on cellular adhesion-induced deformation of compliant substrata. *Phys Rev E* 78: 041923.

Nicolas A (2017) Cell adhesion mechanosensitivity, an active biological process—comment on "Cellular mechanosensing of the biophysical microenvironment: a review of the mathematical models of biophysical regulation of cell responses" by Bo Cheng et al. *Phys Life Rev* 22-23: 123-126.

Park J Y, Lee D H, Lee E J, Lee S H (2009) Study of cellular behaviors on concave and convex microstructures fabricated from elastic PDMS membranes. *Lab Chip* 9: 2043-2049.

Przekora A (2019) The summary of the most important cell-biomaterial interactions that need to be considered during in vitro biocompatibility testing of bone scaffolds for tissue engineering applications. *Mat Sci Eng C* 97: 1036-1051.

Rape A D, Guo W-H, Wang Y-L (2011) The regulation of traction force in relation to cell shape and focal adhesions. *Biomaterials* 32: 2043-2051.

Rodriguez M L, McGarry P J, Sniadecki N J (2013) Review on cell mechanics: experimental and modeling approaches. *Appl Mech Rev* 65: 060801.

Sanz-Herrera J A, Moreo P, Garcia-Aznar J M, Doblare M (2009) On the effect of substrate curvature on cell mechanics. *Biomaterials* 30: 6674-6686.

Soine J R D, Hersch N, Dreissen G, Hampe N, Hoffmann B, et al. (2016) Measuring cellular traction forces on nonplanar substrates. *Interface Focus* 6: 20160024.

Song L, Wang K, Li Y, Yang Y (2016) Nanotopography promoted neuronal differentiation of humaninduced pluripotent stem cells. *Colloids Surf B Biointerfaces* 148: 49-58.

Song W, Kawazoe N, Chen G (2011) Dependence of spreading and differentiation of mesenchymal stem cells on micropatterned surface area. *J Nanomater* 2011: 265251.

Soscia D A, Sequeira S J, Schramma R A, Jayarathanam K, Cantara S I, et al. (2013) Salivary gland cell differentiation and organization on micropatterned PLGA nanofiber craters. *Biomaterials* 34: 6773-6784.

Spill F, Zaman M H (2017) Multiscale dynamics of the biophysical and biochemical microenvironment—Comment on "Cellular mechanosensing of the biophysical microenvironment: a review of mathematical models of biophysical regulation of cell responses" by Bo Cheng et al. *Phys Life Rev* 22-23: 127-129.

Subramaniam A, Sethuraman S, Chapter 18: Biomedical Applications of Nondegradable Polymers. In "Natural and Synthetic Biomedical Polymers", Edited by Kumbar S G, Laurencin C T, Deng M, Elsevier, Amsterdam, *Netherlands,* 2014, 301-308.

Swift J, Ivanovska I L, Buxboim A, Harada T, Dingal PCDP, et al. (2013) Nuclear lamin-A scales with tissue stiffness and enhances matrix-directed differentiation. *Science* 341: 1240104.

Tang X, Ali M Y, Saif M T A (2012) A novel technique for micro-patterning proteins and cells on polyacrylamide gels. *Soft Matter* 8: 7197-7206.

Tang X, Wen Q, Kuhlenschmidt T B, Kuhlenschmidt M S, Janmey P A, et al. (2012) Attenuation of cell mechanosensitivity in colon cancer cells during in vitro metastasis. *PLoS ONE* 7:e50443.

Vassaux M, Milan J L (2017) Stem cell mechanical behaviour modelling: substrate's curvature influence during adhesion. *Biomech Model Mechanobiol* 16: 1295-1308.

Vega S L, Arvind V, Mishra P, Kohn J, Murthy N S, et al. (2018) Substrate micropatterns produced by polymer demixing regulate focal adhesions, actin anisotropy, and lineage differentiation of stem cells. *Acta Biomaterialia* 76: 21-28.

Velmurugan B K, Priya L B, Poornima P, Lee L-J, Baskaran R (2019) Biomaterial aided differentiation and maturation of induced pluripotent stem cells. *J Cell Physiol* 234: 8443-8454.

Vining K H, Mooney D J (2017) Mechanical forces direct stem cell behaviour in development and regeneration. *Nat Rev Mol Cell Bio* 18: 728-742.

von Erlach T C, Bertazzo S, Wozniak M A, Horejs C-M, Maynard S A, et al. (2018) Cell-geometry-dependent changes in plasma membrane order direct stem cell signaling and fate. *Nat Mater* 17: 237-242.

Wan L Q, Kang S M, Eng G, Grayson W L, Lu X L, et al. (2010) Geometric control of human stem cell morphology and differentiation. *Integr Biol* 2: 346-353.

Wang Y L, Pelham R J (1998) Preparation of a flexible, porous polyacrylamide substrate for mechanical studies of cultured cell. *Methods in Enzym* 298: 489-496.

Werner M, Blanquer S B G, Haimi S P, Korus G, Dunlop J W C, et al. (2017) Surface curvature differentially regulates stem cell migration and differentiation via altered attachment morphology and nuclear deformation. *Adv Sci* 4: 1600347.

Winkler T, Sass F A, Duda G N, Schmidt-Bleek K (2018) A review of biomaterials in bone defect healing, remaining shortcomings and future opportunities for bone tissue engineering. *Bone Joint Res* 7, 232-243.

Wu J, LeDuc P, Steward R (2017) How can we predict cellular mechanosensation?—comment on "Cellular mechanosensing of the biophysical microenvironment: a review of mathematical models of biophysical regulation of cell responses" by Bo Cheng et al. *Phys Life Rev* 22-23: 120-122.

Yao X, Peng R, Ding J (2013) Effects of aspect ratios of stem cells on lineage commitments with and without induction media. *Biomaterials* 34: 930-939.

Zadpoor A (2015) Bone tissue regeneration: the role of scaffold geometry. *Biomater Sci* 3: 231-245.

Zhang L, Yang G, Johnson B N, Jia X (2019) Three-dimensional (3D) printed scaffold and material selection for bone repair. *Acta Biomater* 84: 16-33.

Zhang X-Y, Fang G, Zhou J (2017) Additively manufactured scaffolds for bone tissue engineering and the prediction of their mechanical behavior: a review. *Materials* 10: 50.

Zhao C, Wang X, Gao L, Jing L, Zhou Q, et al. (2018) The role of the micro-pattern and nano-topography of hydroxyapatite bioceramics on stimulating osteogenic differentiation of mesenchymal stem cells. *Acta Biomaterialia* 73: 509-521.

What is claimed is:

1. A method of fabricating curvature-defined (C-D) or shape-defined (S-D) concave and convex surfaces for use in cell and tissue culturing and in other surface and interface applications, comprising:

(1) setting rigid C-D or S-D convex microstructures in a fluidic first material layer, wherein the thickness of the fluidic first material layer is determined by the needed emerging-out heights of the rigid C-D or S-D convex microstructures from the surface of the fluidic first material layer; adding a solidifier to the fluidic first material layer to solidify the fluidic first material layer to immobilize or to embed the rigid C-D or S-D convex microstructures; carefully-removing the immobilized or embedded rigid C-D or S-D convex microstructures from the solidified first material layer to obtain exposed C-D or S-D concave surfaces on the solidified first material layer, wherein the curvatures of the obtained exposed C-D or S-D concave surfaces are exactly opposite to those of the C-D or S-D convex surfaces of the corresponding removed rigid convex microstructures that generated the exposed C-D or S-D concave surfaces;

(2) casting a fluidic second material layer onto the solidified first material layer embedded with rigid C-D or S-D convex microstructures obtained in (1) to cover the rigid C-D or S-D convex microstructures emerging-out from the surface of the solidified first material layer; adding a solidifier to the fluidic second material layer to solidify the fluidic second material layer; carefully-peeling off the upper newly-solidified second material layer from the bottom first material layer, wherein the peeled-off upper solidified second material layer is a fabricated substrate having C-D or S-D concave surfaces, wherein the curvatures of the C-D or S-D concave surfaces of the peeled-off upper second material layer are exactly opposite to those of the C-D or S-D convex surfaces of the corresponding rigid convex microstructures, embedded on the first material layer, which generated these C-D or S-D concave surfaces;

(3) casting a fluidic third material layer onto the first material layer having C-D or S-D concave surfaces obtained in (1), or casting a fluidic third material layer onto the second material layer having C-D or S-D concave surfaces obtained in (2); adding a solidifier to the fluidic third material layer to solidify the fluidic third material layer; carefully-peeling off the upper newly-solidified third material layer from the bottom first material layer obtained in (1) or from the bottom second material layer obtained in (2), wherein the peeled-off upper solidified third material layer is a fabricated substrate having C-D or S-D convex surfaces, wherein the curvatures of the C-D or S-D convex surfaces of the newly-obtained substrate are exactly opposite to those of the corresponding C-D or S-D concave surfaces, obtained in (1) or (2), which generated these C-D or S-D convex surfaces, and wherein the newly-obtained substrate having C-D or S-D convex surfaces is entirely made of a same material, which is in contrast with the above first material layer in (1) embedded with rigid C-D or S-D convex microstructures where the C-D or S-D convex surfaces are from the embedded rigid C-D or S-D convex microstructures, and the material or materials of the embedded rigid C-D or S-D convex microstructures and the material of the first material layer are different;

(4) carefully-removing some of the embedded rigid C-D or S-D convex microstructures from the above first material layer in (1) embedded with rigid C-D or S-D convex microstructures and keeping the rest of the embedded rigid C-D or S-D convex microstructures to obtain a substrate having both C-D or S-D concave and convex surfaces, wherein the curvatures of the obtained exposed C-D or S-D concave surfaces are exactly opposite to those of the C-D or S-D convex surfaces of the corresponding removed rigid convex microstructures that generated these exposed C-D or S-D concave surfaces, and wherein the C-D or S-D convex surfaces of the obtained substrate having both C-D or S-D concave and convex surfaces are from the remaining embedded rigid C-D or S-D convex microstructures;

(5) using a casting-onto and peeling-off fabrication process, described above in (2) and (3), onto the above-obtained substrate having both C-D or S-D concave and convex surfaces in (4) to fabricate a substrate having both C-D or S-D convex and concave surfaces, wherein the newly-obtained substrate having both C-D or S-D convex and concave surfaces is entirely made of a same material, which is in contrast with the above-obtained substrate having both C-D or S-D concave and convex surfaces in (4) where the C-D or S-D convex surfaces are from the embedded rigid C-D or S-D convex microstructures whose material or materials are different from the material of the obtained exposed C-D or S-D concave surfaces which is the material of the above first material layer in (1);

(6) repeatedly using the casting-onto and peeling-off fabrication process onto the above-obtained substrate having C-D or S-D convex surfaces in (3), and onto the above-obtained substrate having both C-D or S-D convex and concave surfaces in (5), to copy the shapes and curvatures of the original C-D or S-D convex and concave surfaces and to obtain new substrates having C-D or S-D concave surfaces, having C-D or S-D convex surfaces, and having both C-D or S-D concave and convex surfaces that are entirely made of same materials.

2. The method of claim 1, wherein the embedded rigid C-D or S-D convex microstructures are rigid C-D or S-D convex spherical microstructures.

3. The method of claim 2, wherein the embedded rigid C-D or S-D convex spherical microstructures comprise diameters of between about one nanometer and about several centimeters or above.

4. The method of claim 1, wherein the embedded rigid C-D or S-D convex microstructures are rigid balls.

5. The method of claim 4, wherein the embedded rigid balls are glass balls.

6. The method of claim 1, wherein the rigid C-D or S-D convex microstructures are embedded on the solidified first material layer as an array or arrays, or as a micro-array or micro-arrays, or as a pattern or patterns, or as a micro-pattern or micro-patterns.

7. The method of claim 1, wherein the embedded rigid C-D or S-D convex microstructures are selected from the group consisting of rigid C-D or S-D convex oval microstructures, rigid C-D or S-D convex elliptical microstructures, rigid C-D or S-D convex cylindrical microstructures, rigid C-D or S-D convex circular microstructures, rigid C-D or S-D convex square microstructures, rigid C-D or S-D convex rectangular microstructures, and combinations thereof.

8. The method of claim 1, wherein the obtained C-D or S-D concave and convex surfaces comprise a coating selected from the group consisting of a cell adhesive, a cell adhesion-promotor, a cell repellent, or a combination thereof.

9. A method of fabricating C-D or S-D concave and convex polydimethylsiloxane (PDMS) surfaces for use in cell and tissue culturing and in other surface and interface applications, comprising:

(1) setting rigid C-D or S-D convex microstructures in a fluidic first PDMS material layer, made of a mixture of the precursor and crosslinker of PDMS at an appropriate ratio, wherein the thickness of the fluidic first material layer is determined by the needed emerging-out heights of the rigid C-D or S-D convex microstructures from the surface of the fluidic first material layer; curing the fluidic PDMS mixture to solidify the fluidic first material layer to immobilize or to embed the rigid C-D or S-D convex microstructures; carefully-removing the immobilized or embedded rigid C-D or S-D convex microstructures from the solidified first PDMS material layer to obtain exposed C-D or S-D concave PDMS surfaces on the solidified first PDMS material layer, wherein the curvatures of the obtained exposed C-D or S-D concave PDMS surfaces are exactly opposite to those of the C-D or S-D convex surfaces of the corresponding removed rigid convex microstructures that generated the exposed C-D or S-D concave PDMS surfaces;

(2) casting a fluidic second PDMS material layer, made of a mixture of the precursor and crosslinker of PDMS at an appropriate ratio, onto the solidified first PDMS material layer embedded with rigid C-D or S-D convex microstructures obtained in (1) to cover the rigid C-D or S-D convex microstructures emerging-out from the surface of the solidified first PDMS material layer; curing the fluidic second PDMS material layer to solidify the fluidic second PDMS material layer; carefully-peeling off the upper newly-solidified second PDMS material layer from the bottom first PDMS material layer, wherein the peeled-off upper solidified second PDMS material layer is a fabricated PDMS substrate having C-D or S-D concave PDMS surfaces, wherein the curvatures of the C-D or S-D concave PDMS surfaces of the peeled-off upper second PDMS material layer are exactly opposite to those of the C-D or S-D convex surfaces of the corresponding rigid convex microstructures, embedded on the first PDMS material layer, which generated these C-D or S-D concave PDMS surfaces;
(3) casting a fluidic third PDMS material layer, made of a mixture of the precursor and crosslinker of PDMS at an appropriate ratio, onto the first PDMS material layer having C-D or S-D concave PDMS surfaces obtained in (1), or casting a fluidic third PDMS material layer onto the second PDMS material layer having C-D or S-D concave PDMS surfaces obtained in (2); curing the fluidic third PDMS material layer to solidify the fluidic third PDMS material layer; carefully-peeling off the upper newly-solidified third PDMS material layer from the bottom first PDMS material layer obtained in (1) or from the bottom second PDMS material layer obtained in (2), wherein the peeled-off upper solidified third PDMS material layer is a fabricated PDMS substrate having C-D or S-D convex PDMS surfaces, wherein the curvatures of the C-D or S-D convex PDMS surfaces of the newly-obtained PDMS substrate are exactly opposite to those of the corresponding C-D or S-D concave PDMS surfaces, obtained in (1) or (2), which generated these C-D or S-D convex PDMS surfaces, and wherein the newly-obtained PDMS substrate having C-D or S-D convex PDMS surfaces is entirely made of a same PDMS material, which is in contrast with the above first PDMS material layer in (1) embedded with rigid C-D or S-D convex microstructures where the C-D or S-D convex surfaces are from the embedded rigid C-D or S-D convex microstructures, and the material or materials of the embedded rigid C-D or S-D convex microstructures and the material of the first PDMS material layer are different;
(4) carefully-removing some of the embedded rigid C-D or S-D convex microstructures from the above first PDMS material layer in (1) embedded with rigid C-D or S-D convex microstructures and keeping the rest of the embedded rigid C-D or S-D convex microstructures to obtain a substrate having both C-D or S-D concave and convex surfaces, wherein the curvatures of the obtained exposed C-D or S-D concave PDMS surfaces are exactly opposite to those of the C-D or S-D convex surfaces of the corresponding removed rigid convex microstructures that generated these exposed C-D or S-D concave PDMS surfaces, and wherein the C-D or S-D convex surfaces of the obtained substrate having both C-D or S-D concave and convex surfaces are from the remaining embedded rigid C-D or S-D convex microstructures;
(5) using a casting-onto and peeling-off fabrication process, described above in (2) and (3), onto the above-obtained substrate having both C-D or S-D concave and convex surfaces in (4) to fabricate a PDMS substrate having both C-D or S-D convex and concave PDMS surfaces, wherein the newly-obtained PDMS substrate having both C-D or S-D convex and concave PDMS surfaces is entirely made of a same PDMS material, which is in contrast with the above-obtained substrate having both C-D or S-D concave and convex surfaces in (4) where the C-D or S-D convex surfaces are from the embedded rigid C-D or S-D convex microstructures whose material or materials are different from the material of the obtained exposed C-D or S-D concave PDMS surfaces which is the material of the above first PDMS material layer in (1), (6) repeatedly using the casting-onto and peeling-off fabrication process onto the above-obtained PDMS substrate having C-D or S-D convex PDMS surfaces in (3), and onto the above-obtained PDMS substrate having both C-D or S-D convex and concave PDMS surfaces in (5), to copy the shapes and curvatures of the original C-D or S-D convex and concave PDMS surfaces and to obtain new PDMS substrates having C-D or S-D concave PDMS surfaces, having C-D or S-D convex PDMS surfaces, and having both C-D or S-D concave and convex PDMS surfaces that are entirely made of same materials.

10. The method of claim 9, wherein the embedded rigid C-D or S-D convex microstructures are rigid C-D or S-D convex spherical microstructures.

11. The method of claim 10, wherein the embedded rigid C-D or S-D convex spherical microstructures comprise diameters of between about one nanometer and about several centimeters or above.

12. The method of claim 9, wherein the embedded rigid C-D or S-D convex microstructures are rigid balls.

13. The method of claim 12, wherein the embedded rigid balls are glass balls.

14. The method of claim 9, wherein the rigid C-D or S-D convex microstructures are embedded on the solidified first PDMS material layer as an array or arrays, or as a micro-array or micro-arrays, or as a pattern or patterns, or as a micro-pattern or micro-patterns.

15. The method of claim 9, wherein the embedded rigid C-D or S-D convex microstructures are selected from the group consisting of rigid C-D or S-D convex oval microstructures, rigid C-D or S-D convex elliptical microstructures, rigid C-D or S-D convex cylindrical microstructures, rigid C-D or S-D convex circular microstructures, rigid C-D or S-D convex square microstructures, rigid C-D or S-D convex rectangular microstructures, and combinations thereof.

16. The method of claim 9, wherein the obtained C-D or S-D concave and convex surfaces comprise a coating selected from the group consisting of a cell adhesive, a cell adhesion-promotor, a cell repellent, or a combination thereof.

17. A method of fabricating C-D or S-D concave and convex spherical PDMS surfaces for use in cell and tissue culturing and in other surface and interface applications, comprising:
(1) setting rigid C-D or S-D convex spherical microstructures in a fluidic first PDMS material layer, made of a mixture of the precursor and crosslinker of PDMS at an appropriate ratio, wherein the thickness of the fluidic first material layer is determined by the needed emerging-out heights of the rigid C-D or S-D convex spherical microstructures from the surface of the fluidic first material layer; curing the fluidic PDMS mixture to solidify the fluidic first material layer to immobilize or to embed the rigid C-D or S-D convex spherical microstructures; carefully-removing the immobilized or embedded rigid C-D or S-D convex spherical microstructures from the solidified first PDMS material layer to obtain exposed C-D or S-D concave spherical PDMS surfaces on the solidified first PDMS material layer, wherein the curvatures of the obtained exposed C-D or S-D concave spherical PDMS surfaces are exactly opposite to those of the C-D or S-D convex spherical surfaces of the corresponding removed rigid convex spherical microstructures that generated the exposed C-D or S-D concave spherical PDMS surfaces;

(2) casting a fluidic second PDMS material layer, made of a mixture of the precursor and crosslinker of PDMS at an appropriate ratio, onto the solidified first PDMS material layer embedded with rigid C-D or S-D convex spherical microstructures obtained in (1) to cover the rigid C-D or S-D convex spherical microstructures emerging-out from the surface of the solidified first PDMS material layer; curing the fluidic second PDMS material layer to solidify the fluidic second PDMS material layer; carefully-peeling off the upper newly-solidified second PDMS material layer from the bottom first PDMS material layer, wherein the peeled-off upper solidified second PDMS material layer is a fabricated PDMS substrate having C-D or S-D concave spherical PDMS surfaces, wherein the curvatures of the C-D or S-D concave spherical PDMS surfaces of the peeled-off upper second PDMS material layer are exactly opposite to those of the C-D or S-D convex spherical surfaces of the corresponding rigid convex spherical microstructures, embedded on the first PDMS material layer, which generated these C-D or S-D concave spherical PDMS surfaces;

(3) casting a fluidic third PDMS material layer, made of a mixture of the precursor and crosslinker of PDMS at an appropriate ratio, onto the first PDMS material layer having C-D or S-D concave spherical PDMS surfaces obtained in (1), or casting a fluidic third PDMS material layer onto the second PDMS material layer having C-D or S-D concave spherical PDMS surfaces obtained in (2); curing the fluidic third PDMS material layer to solidify the fluidic third PDMS material layer; carefully-peeling off the upper newly-solidified third PDMS material layer from the bottom first PDMS material layer obtained in (1) or from the bottom second PDMS material layer obtained in (2), wherein the peeled-off upper solidified third PDMS material layer is a fabricated PDMS substrate having C-D or S-D convex spherical PDMS surfaces, wherein the curvatures of the C-D or S-D convex spherical PDMS surfaces of the newly-obtained PDMS substrate are exactly opposite to those of the corresponding C-D or S-D concave spherical PDMS surfaces, obtained in (1) or (2), which generated these C-D or S-D convex spherical PDMS surfaces, and wherein the newly-obtained PDMS substrate having C-D or S-D convex spherical PDMS surfaces is entirely made of a same PDMS material, which is in contrast with the above first PDMS material layer in (1) embedded with rigid C-D or S-D convex spherical microstructures where the C-D or S-D convex spherical surfaces are from the embedded rigid C-D or S-D convex spherical microstructures, and the material or materials of the embedded rigid C-D or S-D convex spherical microstructures and the material of the first PDMS material layer are different;

(4) carefully-removing some of the embedded rigid C-D or S-D convex spherical microstructures from the above first PDMS material layer in (1) embedded with rigid C-D or S-D convex spherical microstructures and keeping the rest of the embedded rigid C-D or S-D convex spherical microstructures to obtain a substrate having both C-D or S-D concave and convex spherical surfaces, wherein the curvatures of the obtained exposed C-D or S-D concave spherical PDMS surfaces are exactly opposite to those of the C-D or S-D convex spherical surfaces of the corresponding removed rigid convex spherical microstructures that generated these exposed C-D or S-D concave spherical PDMS surfaces, and wherein the C-D or S-D convex spherical surfaces of the obtained substrate having both C-D or S-D concave and convex spherical surfaces are from the remaining embedded rigid C-D or S-D convex spherical microstructures;

(5) using a casting-onto and peeling-off fabrication process, described above in (2) and (3), onto the above-obtained substrate having both C-D or S-D concave and convex spherical surfaces in (4) to fabricate a PDMS substrate having both C-D or S-D convex and concave spherical PDMS surfaces, wherein the newly-obtained PDMS substrate having both C-D or S-D convex and concave spherical PDMS surfaces is entirely made of a same PDMS material, which is in contrast with the above-obtained substrate having both C-D or S-D concave and convex spherical surfaces in (4) where the C-D or S-D convex spherical surfaces are from the embedded rigid C-D or S-D convex spherical microstructures whose material or materials are different from the material of the obtained exposed C-D or S-D concave spherical PDMS surfaces which is the material of the above first PDMS material layer in (1);

(6) repeatedly using the casting-onto and peeling-off fabrication process onto the above-obtained PDMS substrate having C-D or S-D convex spherical PDMS surfaces in (3), and onto the above-obtained PDMS substrate having both C-D or S-D convex and concave spherical PDMS surfaces in (5), to copy the shapes and curvatures of the original C-D or S-D convex and concave spherical PDMS surfaces and to obtain new PDMS substrates having C-D or S-D concave spherical PDMS surfaces, having C-D or S-D convex spherical PDMS surfaces, and having both C-D or S-D concave and convex spherical PDMS surfaces that are entirely made of same materials.

18. The method of claim 17, wherein the rigid C-D or S-D convex spherical microstructures are embedded on the solidified first PDMS material layer as an array or arrays, or as a micro-array or micro-arrays, or as a pattern or patterns, or as a micro-pattern or micro-patterns.

19. The method of claim 17, wherein the embedded rigid C-D or S-D convex spherical microstructures are rigid balls.

20. The method of claim 19, wherein the embedded rigid balls are glass balls.

* * * * *